(12) United States Patent
Qin et al.

(10) Patent No.: US 11,331,282 B2
(45) Date of Patent: May 17, 2022

(54) OPHTHALMIC COMPOSITION CONTAINING CLATHRATED ANTIOXIDANT SUBSTANCE, AND USE THEREOF

(71) Applicants: TK Health Research, Co. Ltd., Osaka (JP); THE UNIVERSITY OF TOKYO, Tokyo (JP)

(72) Inventors: Junwen Qin, Tokyo (JP); Yuji Takahashi, Osaka (JP); Shigeru Kakuta, Tokyo (JP); Shigeru Kyuwa, Tokyo (JP)

(73) Assignees: TK Health Research, Co, Ltd.; THE UNIVERSITY OF TOKYO

( * ) Notice: Subject to any disclaimer, the term of this patent is extended or adjusted under 35 U.S.C. 154(b) by 258 days.

(21) Appl. No.: 16/625,053

(22) PCT Filed: Jun. 22, 2018

(86) PCT No.: PCT/JP2018/023780
§ 371 (c)(1),
(2) Date: Dec. 20, 2019

(87) PCT Pub. No.: WO2018/235939
PCT Pub. Date: Dec. 27, 2018

(65) Prior Publication Data
US 2020/0138742 A1    May 7, 2020

(30) Foreign Application Priority Data

Jun. 23, 2017   (JP) .............................. JP2017-123224

(51) Int. Cl.
| A61K 31/122 | (2006.01) |
| A61K 47/40 | (2006.01) |
| A61K 9/08 | (2006.01) |
| A61K 9/00 | (2006.01) |

(52) U.S. Cl.
CPC .......... *A61K 31/122* (2013.01); *A61K 9/0048* (2013.01); *A61K 9/08* (2013.01); *A61K 47/40* (2013.01)

(58) Field of Classification Search
CPC ...... A61K 31/122; A61K 9/0048; A61K 9/08; A61K 47/40
USPC .......................................................... 514/690
See application file for complete search history.

(56) References Cited

U.S. PATENT DOCUMENTS

2005/0051483 A1   3/2005  Majeed et al.

FOREIGN PATENT DOCUMENTS

| JP | 2007-505040 A | 3/2007 |
| JP | 2010-65014 A | 3/2010 |
| JP | 2015-27980 A | 2/2015 |
| JP | 2016-034918 A | 3/2016 |
| WO | 2016057871 A1 | 4/2016 |

OTHER PUBLICATIONS

International Search Report for related International Application No. PCT/JP2018/023780 dated Jul. 19, 2018.
Indian Office Action dated Jun. 23, 2020.

*Primary Examiner* — Kristin A Vajda
(74) *Attorney, Agent, or Firm* — Yokoi & Co., U.S.A.; Toshiyuki Yokoi

(57) ABSTRACT

The present invention provides an ophthalmic composition and a use thereof. In one embodiment of the present invention, an ophthalmic composition containing a clathrated antioxidant substance is provided. In some of embodiments of the present invention, a composition for treating or preventing an ophthalmic disease, an ophthalmic disorder or an ophthalmic symptom is provided, wherein the ophthalmic disease, the ophthalmic disorder or the ophthalmic symptom includes, but is not limited to, dry eye or a dry eye-like ophthalmic disease, conjunctivitis, corneal ulcer, age-related macular degeneration, cataract, pseudoexfoliation syndrome, and symptoms in these diseases which can be ameliorated by increasing the quantity of tears and/or goblet cells and/or mucin.

4 Claims, 12 Drawing Sheets

Figure 1  Water-solubilization of astaxanthin

Figure 2 Antioxidant capability of astaxanthin clathrated with cyclodextrin in the presence of oxidative stress Figure 3 Effect of astaxanthin eye drops in dry eye model mouse Fig.4
Numerical change in goblet cells
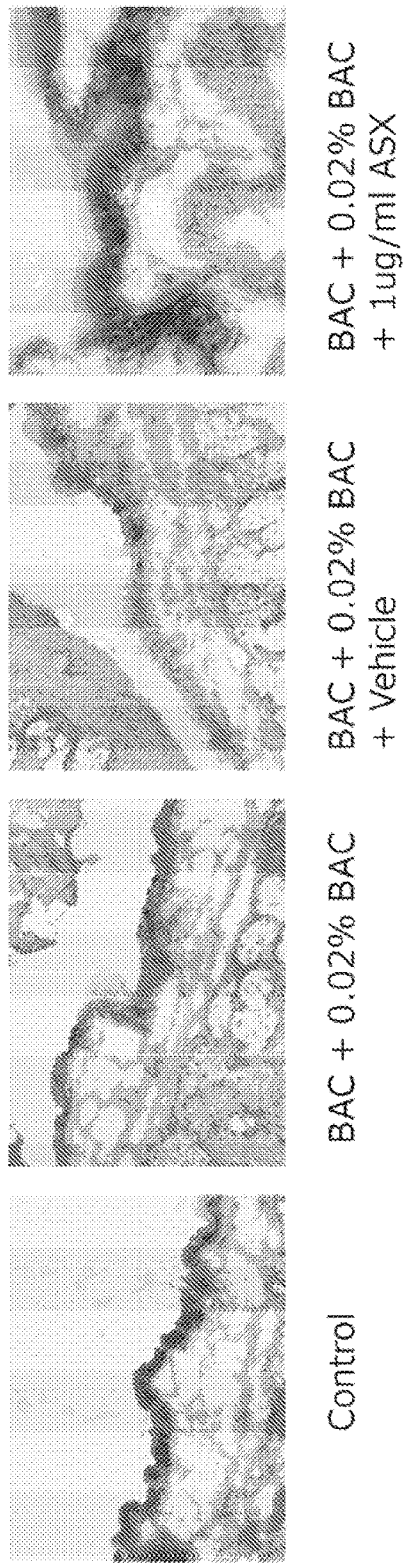
Control | BAC + 0.02% BAC | BAC + 0.02% BAC + Vehicle | BAC + 0.02% BAC + 1ug/ml ASX
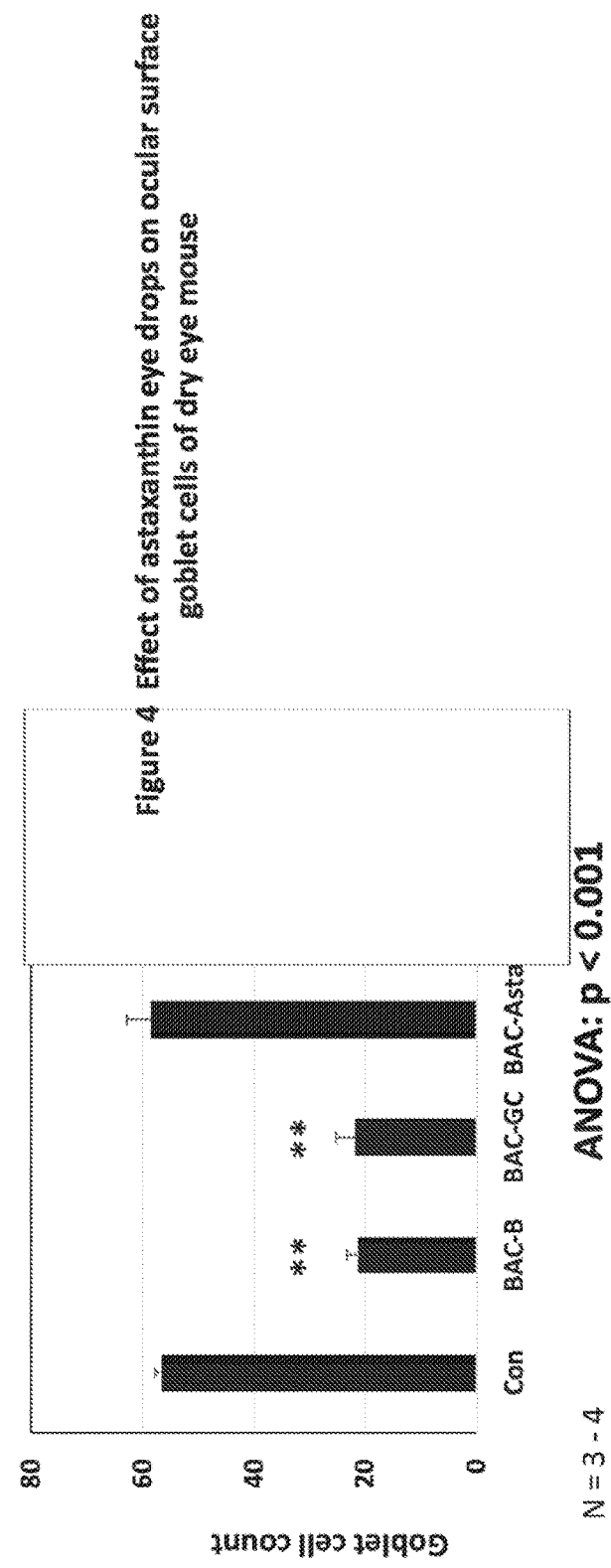
Figure 4 Effect of astaxanthin eye drops on ocular surface goblet cells of dry eye mouse Figure 5 Comparison and examination of improvement in dry eye symptom due to astaxanthin eye drops and oral intake Fig. 6
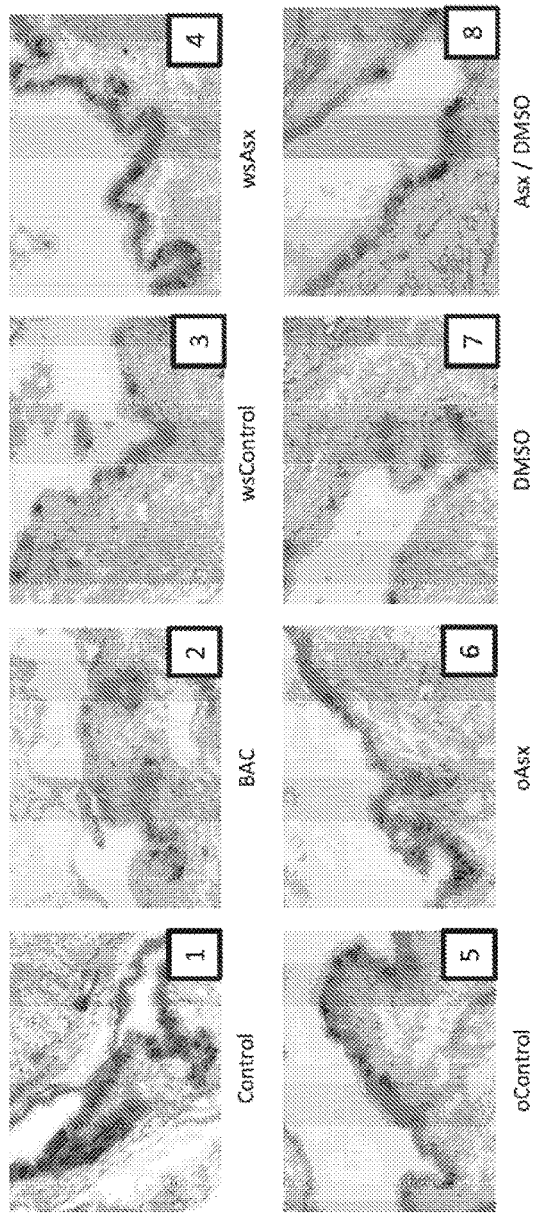
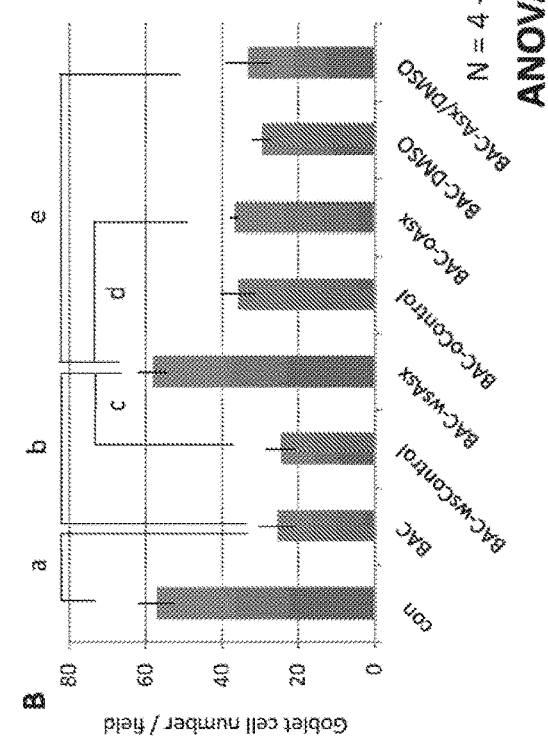
Figure 6 Effect of astaxanthin eye drops on ocular surface goblet cells of dry eye mouse model Figure 7  Effect of ASX dissolved in various solvents on growth in mouse DBT cells Figure 8 Superiority of water-soluble astaxanthin in dry eye mouse Figure 9  Effect of arabinogalactan-ASX clathrate on growth of mouse DBT cells

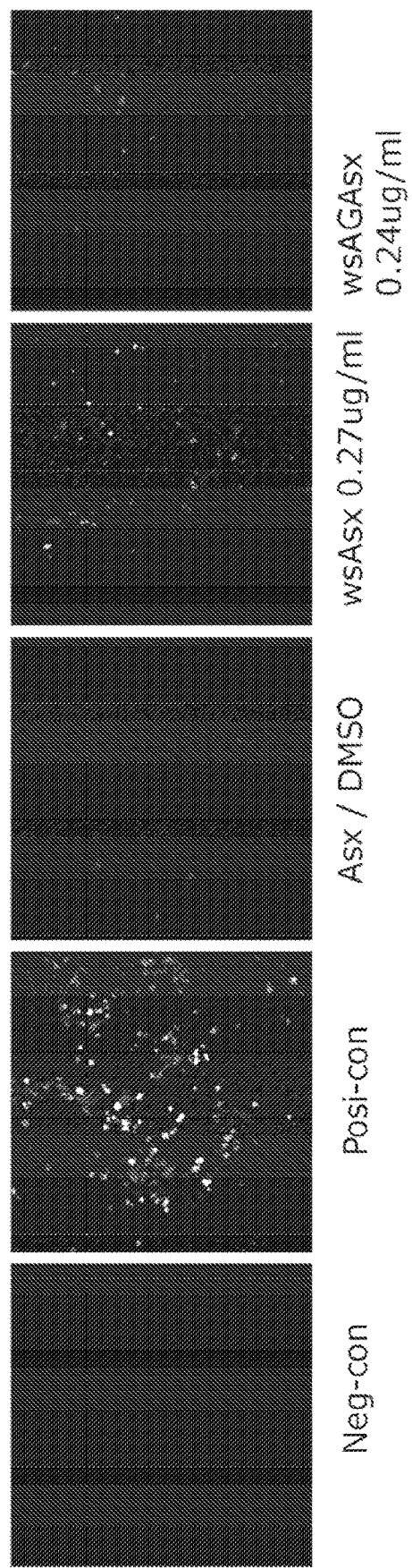
Figure 10 Antioxidant capability of astaxanthin clathrated with arabinogalactan in the presence of oxidative stress

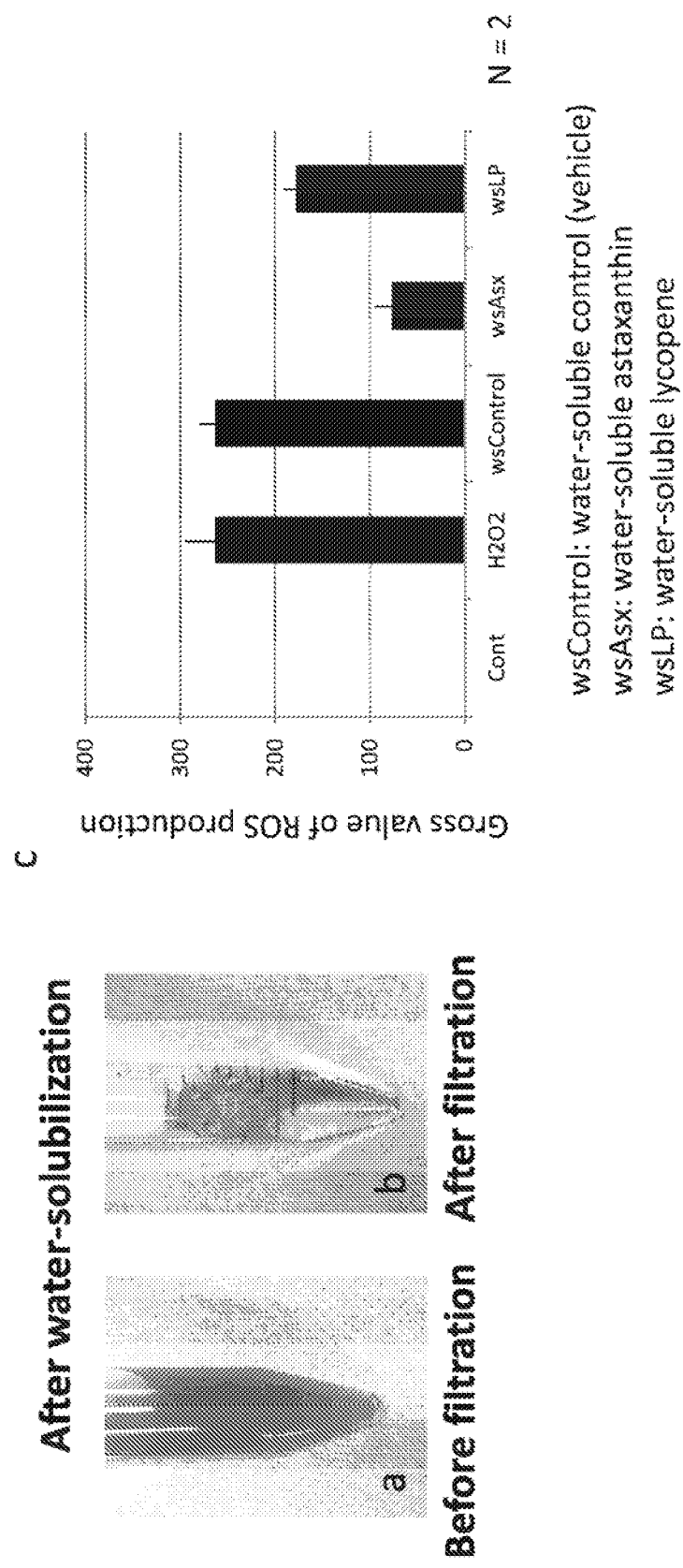
Figure 11 Antioxidant capability of water-soluble lycopene under oxidative stress conditions

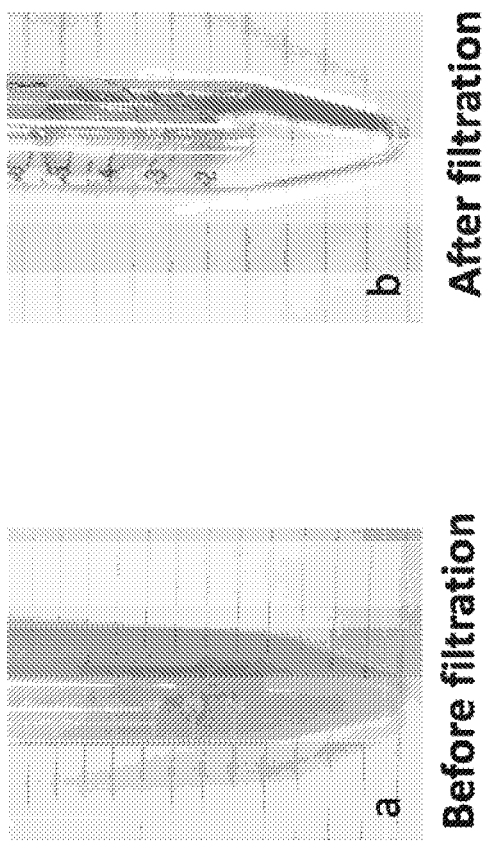
Fig.12 Figure 12 Water-solubilization of canthaxanthin

OPHTHALMIC COMPOSITION CONTAINING CLATHRATED ANTIOXIDANT SUBSTANCE, AND USE THEREOF

TECHNICAL FIELD

The present invention relates to the field of ophthalmic therapy.

BACKGROUND ART

It is understood that reactive oxygen/free radical generated in the body induces a non-specific chemical reaction on various substances, resulting in cell damage. For this reason, there are enzymes in the body that detoxify reactive oxygen species such as catalase as an antioxidant enzyme. To enhance such an antioxidant action, an antioxidant is broadly used as a nutritional supplement or the like.

For example, lipid-soluble antioxidants including astaxanthin are used especially in oral intake applications such as nutritional supplements and supplements.

SUMMARY OF INVENTION

Solution to Problem

The inventors found that clathrating and solubilizing an antioxidant is useful in, for example, drugs, quasi-drugs, cosmetics, food products, and the like. In particular, the inventors found that clathrating and solubilizing an antioxidant is useful in ophthalmic applications. Therefore, one embodiment of the invention is an ophthalmic composition comprising a clathrated antioxidant.

One embodiment of the invention is an ophthalmic composition for increasing the tear volume and/or for increasing the goblet cell count. The inventors found that the composition of the invention is useful in increasing the tear volume and/or increasing the goblet cell count. Some of the embodiments of the invention provide a composition for treating or preventing an ophthalmic disease, ophthalmic disorder, or ophthalmic symptom. Examples of ophthalmic diseases, ophthalmic disorders, or ophthalmic symptoms include, but are not limited to, dry eye or similar ophthalmic diseases, conjunctivitis, corneal ulcer, age-related macular degeneration, cataract, pseudoexfoliation syndrome, symptoms improved by increasing the tear volume and/or goblet cells and/or mucin in such diseases, and the like. Other embodiments provide a composition for recovery of an ocular surface after an invasive ophthalmic procedure such as surgery or cancer therapy. One embodiment provides a composition for treating or preventing an immunological disease including graft-versus-host disease (GVHD), and a symptom or complication (e.g., dry eye or similar ophthalmic disease, ophthalmic disorder, or ophthalmic symptom) that is improved by increasing the tear volume and/or goblet cells and/or mucin in said disease. A preferred embodiment provides an ophthalmic composition for treating or preventing dry eye or a similar ophthalmic disease. For example, the ophthalmic composition of the invention can be provided as an eye infusion, eye ointment, eye drops, or eye irrigating solution.

An antioxidant is preferably a lipid-soluble antioxidant. Examples of lipid-soluble antioxidants include carotenoids (carotenes, xanthophylls, and the like), omega-3 fatty acids (DHA, EPA, and the like), vitamin D (calciferols), vitamin E (tocopherol and tocotrienols), polyphenols (resveratrol and the like), and the like. A lipid-soluble antioxidant is, for example, an antioxidant comprising a conjugated double bond. A lipid-soluble antioxidant is preferably a carotenoid. Examples of lipid-soluble antioxidants include, but are not limited to, astaxanthin, canthaxanthin, zeaxanthin, β-carotene, lutein, lycopene, resveratrol, meso-zeaxanthin, EPA, DHA, curcumin, vitamin E, and the like. A particularly preferable lipid-soluble antioxidant is astaxanthin.

In one embodiment of the invention, it is characterized in that an antioxidant is clathrated. For example, an antioxidant is clathrated with a host compound that is capable of solubilizing the antioxidant. A cyclic polysaccharide can be used as a host compound. Examples of host compounds include, but are not limited to, cyclodextrin, arabinogalactan, glycyrrhizin, hydroxy-beta-cyclodextrin, β1,3-1,6-glucan, calixarene, cavitand, crown ether, calixarene, spherand, sulfobutyl ether-β-cyclodextrin, randomly methylated-β-cyclodextrin, hydroxy-γ-cyclodextrin, epichlorohydrin-β-cyclodextrin, carboxymethyl epichlorohydrin-β-cyclodextrin, and the like. Those skilled in the art understand that any derivative can be used for the host compound in order to adjust the efficiency of clathration or water-solubility.

Preferably, a host compound is a cyclic polysaccharide. The Examples herein demonstrate clathration of a lipid-soluble antioxidant with cyclodextrin or arabinogalactan, which is cyclic polysaccharide.

More preferably, a host compound is cyclodextrin. Examples of cyclodextrin include, but are not limited to, α-cyclodextrin, β-cyclodextrin, and γ-cyclodextrin. Those skilled in the art can select and use a suitable host compound from those described herein, depending on the size of the compound to be clathrated or the like. The size of γ-cyclodextrin can be useful for clathration of a lipid-soluble antioxidant such as astaxanthin.

One aspect of the invention provides an ophthalmic composition comprising a lipid-soluble antioxidant and a macrocyclic compound, wherein water-solubility of the lipid-soluble antioxidant is increased compared to water-solubility for the lipid-soluble antioxidant alone. A lipid-soluble antioxidant can be present in an aqueous solution. The Examples herein demonstrate that it can be useful in ophthalmic therapy to improve the water-solubility (solubilization) of a lipid-soluble antioxidant and dissolve the antioxidant in an aqueous solution. Preferably, a lipid-soluble antioxidant is astaxanthin, and a macrocyclic compound is γ-cyclodextrin. Such a composition can be suitably used for treating or preventing dry eye or a similar ophthalmic disease.

For example, the following items are provided in a preferred embodiment of the invention.

(Item 1)

An ophthalmic composition comprising a clathrated antioxidant.

(Item 2)

The ophthalmic composition of the preceding item, wherein the antioxidant is a lipid-soluble antioxidant.

(Item 3)

The ophthalmic composition of any one of the preceding items, wherein the antioxidant is clathrated with a host compound capable of solubilizing the antioxidant.

(Item 4)

The ophthalmic composition of any one of the preceding items, wherein the host compound is a macrocyclic compound.

(Item 5)

An ophthalmic composition, comprising a lipid-soluble antioxidant and a macrocyclic compound, wherein water-solubility of the lipid-soluble antioxidant is increased compared to water-solubility for the lipid-soluble antioxidant alone.

(Item 6)

The ophthalmic composition of any one of the preceding items for increasing a tear volume.

(Item 7)

The ophthalmic composition of any one of the preceding items for increasing a goblet cell count.

(Item 8)

The ophthalmic composition of any one of the preceding items for increasing mucin.

(Item 9)

The ophthalmic composition of any one of the preceding items for treating an ophthalmic disease, ophthalmic disorder, or ophthalmic symptom, which is treated, improved, or attains reversal in a status by increasing a tear volume.

(Item 10)

The ophthalmic composition of any one of the preceding items for treating an ophthalmic disease, ophthalmic disorder, or ophthalmic symptom, which is treated, improved, or attains reversal in a status by increasing goblet cells.

(Item 11)

The ophthalmic composition of any one of the preceding items for treating an ophthalmic disease, ophthalmic disorder, or ophthalmic symptom, which is treated, improved, or attains reversal in a status by increasing mucin.

(Item 12)

The ophthalmic composition of any one of the preceding items for recovery of an ocular surface after an invasive ophthalmic procedure.

(Item 13)

The ophthalmic composition of any one of the preceding items for treating or preventing dry eye or a similar ophthalmic disease, ophthalmic disorder, or ophthalmic symptom, conjunctivitis, corneal ulcer, age-related macular degeneration, cataract, or pseudoexfoliation syndrome.

(Item 14)

The ophthalmic composition of any one of the preceding items for treating or preventing dry eye or a similar ophthalmic disease, ophthalmic disorder, or ophthalmic symptom in graft-versus-host disease (GVHD).

(Item 15)

The ophthalmic composition of any one of the preceding items, which is an eye drop or an eye irrigating solution.

(Item 16)

The ophthalmic composition of any one of the preceding items, wherein the lipid-soluble antioxidant comprises a conjugated double bond.

(Item 17)

The ophthalmic composition of any one of the preceding items, wherein the lipid-soluble antioxidant is a carotenoid.

(Item 18)

The ophthalmic composition of any one of the preceding items, wherein the lipid-soluble antioxidant is astaxanthin, lutein, canthaxanthin, zeaxanthin, β-carotene, lycopene, resveratrol, meso-zeaxanthin, EPA, DHA, curcumin, or vitamin E.

(Item 19)

The ophthalmic composition of any one of the preceding items, wherein the macrocyclic compound is a cyclic polysaccharide.

(Item 20)

The ophthalmic composition of any one of the preceding items, wherein the macrocyclic compound is cyclodextrin, arabinogalactan, glycyrrhizin, hydroxy-beta-cyclodextrin, β1,3-1,6-glucan, calixarene, cavitand, crown ether, calixarene, spherand, sulfobutyl ether-β-cyclodextrin, randomly methylated-β-cyclodextrin, hydroxy-γ-cyclodextrin, epichlorohydrin-β-cyclodextrin, or carboxymethyl epichlorohydrin-β-cyclodextrin.

(Item 21)

The ophthalmic composition of any one of the preceding items, wherein the macrocyclic compound is γ-cyclodextrin.

(Item 22)

The ophthalmic composition of any one of the preceding items for treating or preventing dry eye or a similar ophthalmic disease, wherein the lipid-soluble antioxidant is astaxanthin and the macrocyclic compound is γ-cyclodextrin.

The present invention is intended so that one or more of the above features can be provided as the explicitly disclosed combinations as well as other combinations thereof. Additional embodiments and advantages of the present invention are recognized by those skilled in the art by reading and understanding the following detailed explanation, as needed.

Advantageous Effects of Invention

The present invention provides a drug that significant improves dry eye or a similar ophthalmic disease, conjunctivitis, corneal ulcer, age-related macular degeneration, or cataract, and symptom improved by increasing the tear volume and/or goblet cells and/or mucin in such diseases, as an ophthalmic disease, ophthalmic disorder, or ophthalmic symptom.

BRIEF DESCRIPTION OF DRAWINGS

FIG. 4 is a diagram showing the effect of astaxanthin eye drop on ocular surface goblet cells of a dry eye mouse model. The top panel shows a tissue segment of each treatment group. The bottom panel shows the goblet cell count in each treatment group found by counting the number of cells stained red by PAS stain in each segment.

FIG. 6 is a diagram showing the effect of water-soluble astaxanthin eye drop, DMSO-dissolved astaxanthin eye drop, and astaxanthin oral administration on the goblet cell count. Panel A on the top shows a tissue segment after each treatment. Panel B on the bottom shows the goblet cell count in each treatment group found by counting the number of cells stained red by PAS stain in each segment.

FIG. 10 is a diagram showing the antioxidant capability of water-soluble astaxanthin using different host compounds. Reactive oxygen species were detected using a DCFDA reagent, and the antioxidant capability of the shown test substances (Neg-con: untreated group, Posi-con: (production of reactive oxygen is detected under hydrogen peroxide stimulation), Asx/DMSO: astaxanthin dissolved in DMSO (5 μg/mL), wsAsx: astaxanthin solubilized by cyclodextrin clathration (0.27 μg/mL), and wsAGAsx: astaxanthin solubilized by arabinogalactan clathration (0.24 μg/mL) was studied. Low fluorescence indicates that the antioxidant capability of a test substance against oxidative stress induced by hydrogen peroxide is high.

FIG. 11 is a diagram showing clathration of lycopene using γ-cyclodextrin and the antioxidant capability of clathrated lycopene. In the figure, "wsControl" is water-soluble control (vehicle), "wsAsx" is water-soluble astaxanthin (ASX), and "wsLP" is water soluble lycopene.

FIG. 12 is a diagram showing clathration of canthaxanthin using γ-cyclodextrin.

DESCRIPTION OF EMBODIMENTS

Figure 1:
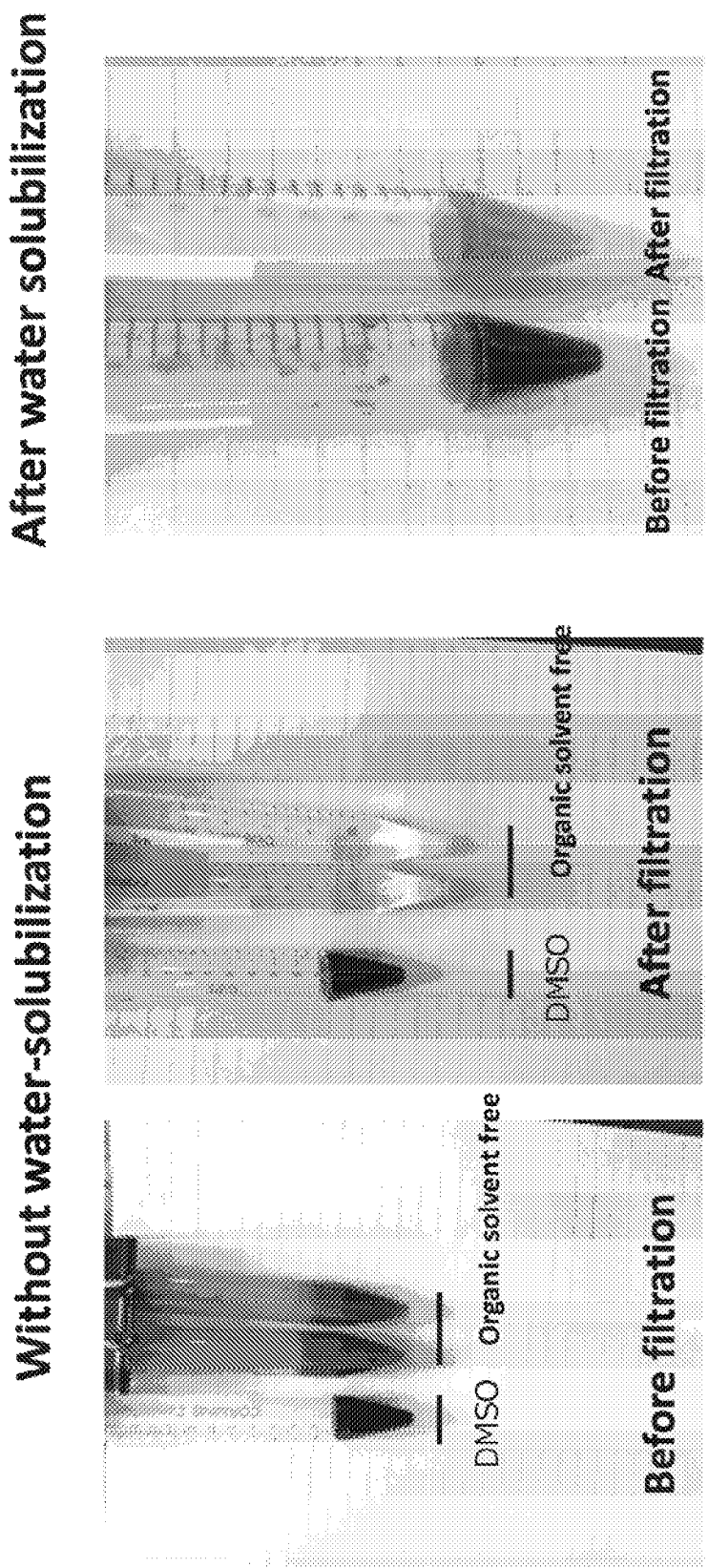
FIG. 1 is a diagram showing solubilization of astaxanthin. Astaxanthin, when not solubilized, is removed from a filtrate by filtration, so that the filtrate becomes colorless.

The present invention is described hereinafter with the best modes of the invention. Throughout the entire specification, a singular expression should be understood as encompassing the concept thereof in a plural form, unless specifically noted otherwise. Thus, singular articles (e.g., "a", "an", "the", and the like in the case of English) should also be understood as encompassing the concept thereof in a plural form, unless specifically noted otherwise. Further, the terms used herein should be understood to be used in the meaning that is commonly used in the art, unless specifically noted otherwise. Thus, unless defined otherwise, all terminologies and scientific technical terms that are used herein have the same meaning as the general understanding of those skilled in the art to which the present invention pertains. In case of a contradiction, the present specification (including the definitions) takes precedence.

The definitions of terms and/or basic technologies that are particularly used herein are described hereinafter when appropriate.

1. Definition

As used herein, "clathrate" refers to a compound taken into a space created by another compound as a stable substance without a covalent bond, where the compound taking in another compound can be referred to as a "host compound", and the compound taken in can be referred to as a "guest compound". A clathrating compound is also referred to as a clathrate or the like, and formation of clathrate is also referred to as "clathration".

As used herein, an "antioxidant" refers to a substance that inhibits an oxidation reaction involving oxygen.

As used herein, "or" is used when "at least one or more" of the listed matters in the sentence can be employed. When explicitly described herein as "within the range" of "two values", the range also includes the two values themselves.

2. Antioxidant

One embodiment of the invention provides a composition comprising an antioxidant. An antioxidant is a substance that inhibits an oxidation reaction involving oxygen, and can function to protect cells from oxidative stress due to reactive oxygen species or the like. The Examples herein show that an increase in tear volume or increase in goblet cell count in a mouse model can be achieved by administration of a clathrated antioxidant as eye drops. It is demonstrated that the tear volume and/or goblet cells and/or mucin can be increased significantly, and an ophthalmic disease, ophthalmic disorder, or ophthalmic symptom can be treated, improved, or prevented based thereon.

Examples of antioxidants include, but are not limited to, superoxide dismutase, glutathione peroxidase, catalase, peroxidase, ascorbic acid, cysteine, glutathione, linoleic acid, tocopherols, tocotrienols, carotenoids, flavonoid, riboflavin, bilirubin, uric acid, lipoic acid, ubiquinol, melatonin, urobilinogen, xanthophylls, polyphenol, and the like. Antioxidants are largely classified into lipid-soluble antioxidants and water-soluble antioxidants. In general, a water-soluble antioxidant reacts with the cytoplasmic matrix and an oxidant in plasma, and a lipid-soluble antioxidant prevents a lipid peroxidation reaction of cell membranes.

In one embodiment, an antioxidant is a lipid-soluble antioxidant. Examples of lipid-soluble antioxidants include carotenoids (carotenes, xanthophylls, and the like), omega-3 fatty acids (DHA, EPA, and the like), vitamin D (calciferols), vitamin E (tocopherol and tocotrienols), and the like. A lipid-soluble antioxidant can be advantageously utilized in drugs or the like by solubilization through clathration.

Carotenoid is a naturally occurring dye and a derivative of a compound with a backbone structure represented by the chemical formula $C_{40}H_{56}$. In particular, carotenoid comprised of only carbon and hydrogen is referred to as carotene, and those comprising oxygen, nitrogen, or the like besides carbon and hydrogen are referred to as xanthophyll. Carotene and xanthophyll have a potent antioxidation action due to comprising many double bonds. In a preferred embodiment of the invention, an antioxidant is a carotenoid because the Examples herein have demonstrated that the tear volume and/or goblet cells and/or mucin can be increased significantly and dry eye can be successfully treated by using clathrated carotenoid.

Examples of carotenoids included in carotenes include, but are not limited to, α-carotene, β-carotene, γ-carotene, δ-carotene, lycopene, ε-carotene, and the like. Examples of carotenoids included in xanthophylls include, but are not limited to, astaxanthin, lutein, canthaxanthin, zeaxanthin, fucoxanthin, antheraxanthin, violaxanthin, meso-zeaxanthin, and the like.

A lipid-soluble antioxidant is, for example, an antioxidant comprising a conjugated double bond. The Examples herein show that an increase in the tear volume or increase in the goblet cell count can be achieved in a mouse model by administration of astaxanthin, which is an antioxidant comprising a conjugated double bond. It is understood that the high antioxidant capability of carotenoid including astaxanthin originates from a conjugated double bond chain in a molecule. Polyenes and conjugated unsaturated fatty acid (conjugated linoleic acid and the like) with a similar conjugated double bond can also be used herein.

In a particularly preferred embodiment of the invention, a lipid-soluble antioxidant is astaxanthin. Astaxanthin has a potent antioxidant action, and is understood to function as an agent protecting the biological body from UV rays or lipid peroxidation reactions.

One aspect of the invention provides a composition wherein water-solubility of a lipid-soluble antioxidant is increased compared to water-solubility for the lipid-soluble antioxidant alone. Such a composition comprises a lipid-soluble antioxidant and any compound that can be used as a host compound described herein. The compound that can be used as a host compound can be a macrocyclic compound described herein, a cyclic polysaccharide described herein, cyclodextrin described herein or a derivative thereof, or the like. Preferably, a lipid-soluble antioxidant is astaxanthin. Preferably, a macrocyclic compound is γ-cyclodextrin.

A lipid-soluble antioxidant can be present in an aqueous solution. A lipid-soluble antioxidant can be present in a state of being dissolved in an aqueous solvent. The Examples herein show that a lipid-soluble antioxidant can be usefully used in ophthalmic therapy by improving the water-solubility (solubilizing) of the antioxidant and dissolving the antioxidant in an aqueous solution. An aqueous solvent is any solvent with water as the primary component, and can comprise any additive described herein, including for example purified water, sterilized water, buffer, and saline.

Water-solubility of a lipid-soluble antioxidant contained in a composition with a compound that can be used as a host compound can increase, for example, at least about 10%, about 30%, about 50%, about 70%, or about 100%, or at least about 1.5-fold, about 2-fold, about 3-fold, about 5-fold, about 10-fold, about 20-fold, about 50-fold, about 100-fold, about 150-fold, about 200-fold, about 300-fold, about 500-fold, or about 1000-fold, or about $10^4$-fold, about $10^5$-fold, about $10^6$-fold, about $10^7$-fold, about $10^8$-fold, about $10^9$-fold, about $10^{10}$-fold, about $10^{11}$-fold, or about $10^{12}$-fold, compared to the lipid-soluble antioxidant alone.

The water-solubility for the lipid-soluble antioxidant alone is known to those skilled in the art as solubility data of a compound. For example, the solubility of astaxanthin is $7.9 \times 10^{-10}$ mg/L=(μg/ml) at 25° C. (https://pubchem.ncbi.nlm.nih.gov/compound/5281224#section=Solubility).

In one embodiment, water-solubility of astaxanthin contained in a composition with a compound that can be used as a host compound can be at least about $1 \times 10^{-9}$ g/ml, about $1 \times 10^{-8}$ μg/ml, about $1 \times 10^{-7}$ μg/ml, about $1 \times 10^{-6}$ μg/ml, about $1 \times 10^{-5}$ μg/ml, about $1 \times 10^{-4}$ μg/ml, about $1 \times 10^{-3}$ μg/ml, about $1 \times 10^{-2}$ μg/ml, about $1 \times 10^{-1}$ μg/ml, about 1 μg/ml, about 5 μg/ml, about 10 μg/ml, about 15 μg/ml, or about 20 μg/ml.

3. Clathration

In one embodiment, it is characterized in that an antioxidant is clathrated. For example, an antioxidant is clathrated with a host compound capable of solubilizing the antioxidant. The Examples herein show that an antioxidant solubilized by clathration unexpectedly improved a dry eye symptom compared to the same antioxidant dissolved in an organic solvent. It is demonstrated that the tear volume and/or goblet cells and/or mucin can be increased significantly, and an ophthalmic disease, ophthalmic disorder, or ophthalmic symptom can be treated, improved, or prevented based thereon.

A lipid-soluble antioxidant, upon use, can be solubilized by emulsification using a surfactant. However, a composition used as, for example, eye drops containing a surfactant would be a risk for cells, so that solubilization by clathration is also advantageous with respect to this point.

A macrocyclic molecule such as a cyclic polysaccharide, crown ether, or calixarene can be used for clathration. Examples of compounds used in clathration include β1,3-1,6-glucan, cavitand, calixarene, spherand, and the like. A host compound with the inside exhibiting lipophilicity and the outside exhibiting hydrophilicity is desirable for solubilization of a lipid-soluble antioxidant.

Although not wishing to be bound by any theory, a host compound can take in a guest molecule by some type of interaction with the guest molecule. The interaction between a host compound and a guest compound is envisioned primarily as a hydrophobic bond or intramolecular bond, but involvement of a hydrogen bond is also envisioned in some cases.

As used herein, a "macrocyclic compound" is a cyclic macromolecule or a macromolecular cyclic moiety of a molecule (e.g., molecule comprising a ring of 9 or more atoms preferably comprising two or more potential donor atoms that can be coordinated to a ligand).

A macrocyclic compound has solubility in an environment wherein the use is intended. A macrocyclic compound is solubilized in a range of pH 5.5 to 8. It is understood that a pharmaceutical composition such as an ophthalmic aqueous composition is generally used in such a pH range. It is desirable that a host compound can solubilize a guest compound within said range. A macrocyclic compound preferably has solubility from neutral to weak alkaline regions (pH 7 to 8).

Although not wishing to be bound by any theory, a macrocyclic compound can be optimal as a host compound by having a cavity within a molecule. In some cases, a host compound and a guest molecule form clathration at a certain composition ratio. In some cases, the diameter of the cavity of a host compound is preferably almost the same size as the molecular diameter of a guest. A host compound can be selected in accordance with the size of a guest molecule. For example, the mean molecular diameter of vitamin E is 0.45 nm. While a combination with α-cyclodextrin with a cavity diameter of about 0.45 nm is preferred, a guest molecule that is larger than the cavity diameter is clathrated in some cases if a molecule has a partially highly hydrophobic moiety.

As used herein, "cyclic polysaccharides" refers to any polysaccharide with a cyclic structure.

Preferably, a host compound is a cyclic polysaccharide. The Examples herein demonstrate clathration of a lipid-soluble antioxidant with cyclodextrin or arabinogalactan, which is a cyclic polysaccharide. Examples of cyclic polysaccharides include cyclodextrin and arabinogalactan as well as any derivative thereof. Examples of cyclodextrin derivatives include sulfobutyl ether-β-cyclodextrin, randomly methylated-β-cyclodextrin, hydroxy-γ-cyclodextrin, epichlorohydrin-β-cyclodextrin, carboxymethyl epichlorohydrin-β-cyclodextrin, and the like.

A guest compound can be stabilized by clathration. A substance that is vulnerable to UV rays, heat, or the like, an unstable substance that is prone to oxidation or hydrolysis, or the like can be stabilized by clathration. Denaturation of an active ingredient can be prevented to enhance preservability. Since an antioxidant can be prone to decomposition by oxidation due to its nature, stabilization by clathration can be useful.

Further, bioavailability can be improved by clathration. When active ingredients are in an aggregated state due to an intermolecular force, the absorbability of an active ingredient to an action site at the molecular level and sustainability of absorption can be improved by blocking the intermolecular force by clathration. When clathrating a substance with a high viscosity by blocking the intermolecular force, the viscosity can be adjusted to facilitate the use thereof.

In one embodiment, a cyclic polysaccharide can be used as a host compound. Examples of host compounds include, but are not limited to, cyclodextrin, arabinogalactan, glycyrrhizin, hydroxy-beta-cyclodextrin, sulfobutyl ether-β-cyclodextrin, randomly methylated-β-cyclodextrin, hydroxy-γ-cyclodextrin, epichlorohydrin-β-cyclodextrin, carboxymethyl epichlorohydrin-β-cyclodextrin, and the like.

Those skilled in the art understand that any derivative of a host compound can be used to adjust the water-solubility or clathration efficiency. Examples of derivatives of cyclodextrin include, but are not limited to, hydroxy-cyclodextrin, amino-cyclodextrin, azide-cyclodextrin, mercapto-cyclodextrin, succinic-cyclodextrin, O-(p-Tos)-cyclodextrin, ethylenediamino-cyclodextrin, polypropylenediamino-cyclodextrin, butanediamino-cyclodextrin, PEGylated cyclodextrin, sulfobutyl ether-β-cyclodextrin, randomly methylated-β-cyclodextrin, hydroxy-γ-cyclodextrin, epichlorohydrin-β-cyclodextrin, carboxymethyl epichlorohydrin-β-cyclodextrin, and the like.

Preferably, a host compound is cyclodextrin. Examples of cyclodextrin include, but are not limited to, α-cyclodextrin, β-cyclodextrin, and γ-cyclodextrin. Those skilled in the art can select and use a suitable host compound from those described herein depending on the size of the compound to be clathrated or the like. The size of γ-cyclodextrin can be useful for clathration of a lipid-soluble antioxidant such as astaxanthin. Examples herein show that an antioxidant solubilized by clathration with cyclodextrin unexpectedly improved a dry eye symptom compared to the same antioxidant dissolved in an organic solvent. It is demonstrated that the tear volume and/or goblet cells and/or mucin can be increased significantly, and an ophthalmic disease, ophthalmic disorder, or ophthalmic symptom can be treated, improved, or prevented based thereon.

Since the cavity of cyclodextrin has a truncated cone shape, the size of a compound that can be clathrated with cyclodextrin of various sizes is relatively wide ranging. α-cyclodextrin is made by six glucose molecules being linked and has a cavity inner diameter of about 0.5 to 0.6 nm, cavity depth of about 0.7 to 0.8 nm, and cavity volume of 0.176 nm$^3$. Generally, a molecule with a size of about a straight chain molecule can be clathrated. β-cyclodextrin is made by seven glucose molecules being linked and has a cavity inner diameter of about 0.7 to 0.8 nm, cavity depth of about 0.7 to 0.8 nm, and cavity volume of 0.346 nm$^3$. Generally, a molecule with a size of about one phenol group can be clathrated. γ-cyclodextrin is made by eight glucose molecules being linked and has a cavity inner diameter of about 0.9 to 1.0 nm, cavity depth of about 0.7 to 0.8 nm, and cavity volume of 0.510 nm$^3$. Generally, a molecule with a size of about two phenol groups can be clathrated.

A method of adjusting the clathration property of a host compound by chemical modification or the like is known in the art (Shoji FUJIWARA, "Bunshi Kozo oyobi Hosetsu Tokusei Chosei wo Mokuteki toshita Shikurodekisutorin no Kagaku Shushoku; Shinsuiseiki to Sosuiseiki no Balansu Izonsei" [Chemical modification of cyclodextrin for adjusting clathration property and molecular structure; balance dependence of hydrophilic group and hydrophobic group] (2013)).

Use of cyclodextrin or a derivative thereof that is not a naturally-occurring cyclodextrin has advantages such as the ability to increase solubility when used as an aqueous solution, the ability to improve cell permeability, and the like compared to naturally-occurring cyclodextrin. Furthermore, generation of a derivative for enabling selective absorption to the ocular cells leads to the effective utilization method of the invention. For example, it is known that water-solubility of hydroxypropyl-γ-cyclodextrin is much better than naturally-occurring forms. Use of a derivative exhibiting high water-solubility is preferable for further enhancing the efficacy of the invention.

A "cyclodextrin derivative" refers to cyclodextrin with one of the functional groups therein modified with a substituent. For cyclodextrin, a hydroxyl group is generally modified. A cyclodextrin derivative is obtained by modifying one or more hydroxyl groups selected from the group consisting of a primary hydroxyl group, i.e., position 6 hydroxyl group, and secondary hydroxyl groups, i.e., position 2 and 3 hydroxyl groups, with a substituent in a saccharide constituting cyclodextrin.

The substituent is not particularly limited and can be appropriately selected depending on the objective. Examples thereof include a hydroxyethyl group, hydroxypropyl group, hydroxybutyl group, hydroxyethoxyethyl group, methyl group, N,N-dimethylaminoethyl group (also referred to as a "DMAE" group), carboxyl group, primary amino group, polyethylene glycol, other water soluble polymers and peptide molecules, and the like. The modification of the hydroxyl group can be a direct modification with the substituent or modification via a linker. The linker is not particularly limited and can be appropriately selected depending on the objective. Examples thereof include a carbamic acid ester bond (—O—CO—NH—), ester bond (—O—CO—), carbonate bond (—O—CO—O—), ether bond (—O—), and the like.

Clathration of a compound can be confirmed by HPLC analysis. Clathration can also be confirmed by analysis using FT-IR (Fourier-transform infrared spectroscopy), differential thermal analysis, X-ray diffractometry, differential pulse voltammetry, NMR (nuclear magnetic resonance), or the like.

4. Application

One embodiment of the invention provides use of a clathrated antioxidant in a specific application, or a composition for a specific application comprising a clathrated antioxidant. The Examples herein demonstrate that clathrating and solubilizing an antioxidant can significantly increase the tear volume and/or goblet cells and/or mucin, and show that this is useful in, for example, drugs, quasi-drugs, cosmetics, food products, and the like.

One preferred embodiment of the invention is an ophthalmic composition comprising a clathrated antioxidant. Examples herein demonstrate that clathrating and solubilizing an antioxidant is particularly useful in ophthalmic applications.

One embodiment of the invention is an ophthalmic composition for increasing a tear volume and/or for increasing a goblet cell count. The inventors found that the composition of the invention is useful in increasing a tear volume and/or goblet cell count and/or increasing mucin.

Tears contribute to physical protection of the surface of an eye ball, as well as protection of an eye from drying (tears prevent drying by covering the surface of an eye), supply of oxygen or nutrient to an eye (since the surface of eyes does not have blood vessels, oxygen or nutrients are transported to cells on the surface of the eyes by tears), prevention of infections (foreign objects that have entered the eye are washed away by tears; tears contain lysozyme that prevents infiltration and infections of microorganisms), curing of injury to the surface of an eye (tears contain components that heal an injury on the surface of an eye), and smoothing of the surface of an eye (tears moisten and smooth out the surface of an eye, so that light is properly diffracted). For this reason, it is effective to increase the tear volume in ophthalmic applications.

Goblet cells have a function of secreting mucin. Examples of the roles of mucin in an eye include retaining tears, lubricating the ocular surface, forming a smooth spherical surface of an eye ball to acquire excellent vision, protecting the ocular surface, and capturing and removing pathogens and debris. For this reason, it is effective to increase goblet cells in ophthalmic applications.

The composition of the invention can simultaneously achieve two such objectives. Although not wishing to be bound by any theory, an effect of increasing the tear volume alone is sometimes not useful for dry eye or similar ophthalmic disease because mucin that retains tears is not increased, while the composition of the invention can be advantageous in terms of being able to simultaneous achieve two or more effects of increasing the tear volume and goblet cell count (and/or mucin).

It is understood that the composition of the invention comprising a clathrated antioxidant having said features is useful in therapy or prevention of an ophthalmic disease with a symptom of reduced tear volume, such as dry eye (keratoconjunctivitis sicca), decreased lacrimal fluid secretion, xerophthalmia, Sjogren's syndrome, (systemic autoimmune disease), or Stevens-Johnson syndrome. It is also reported that a dry eye symptom is manifested from a morphological change in goblet cells in pseudoexfoliation syndrome (Vassilios P. Kozobolis et al., "Study of conjunctival goblet cell morphology and tear film stability in pseudoexfoliation syndrome" Graefe's Arch Clin Exp Ophthalmol (2004) 242: 478-483). It is understood that the composition of the invention is useful in treating, improving, or preventing such a disease characterized by denaturation of goblet cells and a symptom of such a disease (e.g., dry eye symptom).

Since the composition of the invention can be used in normalizing the condition of tears in an eye, it is understood that the composition is useful in therapy or prevention of an ocular disease due to infection, inflammation, or cell denaturation in an eye. Further, since the antioxidant of the invention inhibits the formation of a disulfide bond due to the oxidation of an SH group in the lens protein, it is understood that the antioxidant is useful in the treatment or prevention of cataract. Some embodiments of the invention provide a composition for treating or preventing an ophthalmic disease, ophthalmic disorder, or ophthalmic symptom. Examples of ophthalmic diseases, ophthalmic disorders, or ophthalmic symptoms include, but are not limited to, dry eye and similar ophthalmic diseases, conjunctivitis, corneal ulcer, age-related macular degeneration, cataract, and the like. The composition of the invention can be used in treating or preventing dryness of an eye or a symptom of decreased tear volume in an ophthalmic disease.

Although not wishing to be bound by any theory, it is known that a carotenoid such as lutein or astaxanthin is taken into the retina by oral ingestion thereof and is effective in cataract. It is understood that an effect can also be expected by intake from the outside, which is different from intake of a substance from the inside of the body.

The composition of the invention can be used for recover of the ocular surface as a post-surgical treatment after an invasive ophthalmic procedure. For example, it is reported that the goblet cell density (GCD) decreases after a cataract surgery, resulting in a dry eye symptom (Taehoon Oh et al., "Changes in the tear film and ocular surface after cataract surgery" Jpn J Ophthalmol (2012) 56: 113-118). A decrease in goblet cells is also reported after keratectomy or LASIK (laser in situ keratomileusis) (Ocular surface management of photorefractive keratectomy and laser in situ keratomileusis Albietz, Julie M, PhD; McLennan, Suzanne G, BAppSc (Optom); Lenton, Lee M, FRANZCO, FRACS Journal of Refractive Surgery; November/December 2003; 19, 6; Health & Medical Collection). It is also reported that goblet cells decrease after ophthalmic cancer therapy including radiation therapy or retinal surgery, resulting in a dry eye symptom (Ocular surface management of photorefractive keratectomy and laser in situ keratomileusis Albietz, Julie M, PhD; McLennan, Suzanne G, BAppSc (Optom); Lenton, Lee M, FRANZCO, FRACS Journal of Refractive Surgery; November/December 2003; 19, 6; Health & Medical Collection). It is understood that the composition of the invention can be suitably used for the recovery of the ocular surface after such a procedure by the effect of recovery in the goblet cell count demonstrated in the Examples herein. Examples of an invasive ophthalmic procedure include ophthalmic surgeries such as cataract surgery, vitreoretinal surgery, and LASIK (keratorefractive surgery).

When there is a complication of a dry eye symptom with an immunological disease, the composition of the invention can be used to treat, improve, or prevent immunological diseases and symptoms (e.g., dry eye symptom) improved by increasing the tear volume and/or goblet cells and/or mucin in such diseases. It is reported, for example, that a dry eye symptom is manifested by a decrease in goblet cells in graft-versus-host disease (GVHD) (Claudia Auw-Haedrich et al., "Histological and immunohistochemical characterisation of conjunctival graft vs host disease following haematopoietic stem cell transplantation" Graefe's Arch Clin Exp Ophthalmol (2007) 245: 1001-1007: Edgar M. Espana et al., "Graft versus host disease: clinical evaluation, diagnosis and management" Graefes Arch Clin Exp Ophthalmol (2013) 251: 1257-1266). It is understood that the composition of the invention is useful in treating or preventing immunological diseases including graft-versus-host disease (GVHD) and symptoms or complications (e.g., dry eye or similar ophthalmic disease, ophthalmic disorder, or ophthalmic symptom) improved by increasing the tear volume and/or goblet cells and/or mucin in such diseases.

An increase in the tear volume and an increase in the goblet cell count and/or mucin are very effective for the therapy or prevention of dry eye or a similar ophthalmic disease, ophthalmic disorder, or ophthalmic symptom. In a preferred embodiment, an ophthalmic composition for treating or preventing dry eye or a similar ophthalmic disease, ophthalmic disorder, or ophthalmic symptom is provided.

5. Formulation

The composition of the invention can be formulated and provided in a form that matches the application thereof. For example, the composition of the invention, when it is an ophthalmic composition, can be provided as an eye infusion, eye ointment, eye drops, or eye irrigating solution.

A composition can be formulated into any dosage form such as an aerosol, liquid agent, extract, elixir, capsule, granule, pill, ointment, powder, tablet, solution, suspension, or emulsion. The composition can comprise any pharmaceutically acceptable additive and/or excipient that is known in the art. Examples of additives include, but are not limited to, tonicity adjusting agent, buffer, antifouling agent, cosolvent, and thickener. For example, an ophthalmic composition can be provided in a form of a liquid agent prepared by dissolving an active ingredient into an aqueous solvent (e.g., water).

The composition of the invention can be administered through any suitable route determined by those skilled in the art. The composition can be formulated to be suitable for administration through a route of administration selected from, but not limited to, ocular injection, topical application (including application to an eye), eye drop, intravenous injection, intravenous drip, oral administration, parenteral administration, transdermal administration, and the like.

In general, the composition, drug, therapeutic agent, prophylactic agent, and the like of the invention comprise a therapeutic effective amount of a therapeutic agent or active ingredient, and a pharmaceutically acceptable carrier or excipient. As used herein, "pharmaceutically acceptable" means government regulatory agency-approved or Japanese Pharmacopoeia or other commonly recognized pharmacopoeia-listed for use in animals, more specifically in humans. As used herein, "carrier" refers to a diluent, adjuvant, excipient, or vehicle administered with a therapeutic agent. Such a carrier can be an aseptic liquid such as water or oil, including liquids derived from petroleum, animal, plant, or synthesis, such as, but not limited to, peanut oil, soybean oil, mineral oil, and sesame oil. When a drug is orally administered, water is a preferred carrier. For intravenous administration of a pharmaceutical composition, saline and aqueous dextrose are preferred carriers. Preferably, aqueous saline solution and aqueous dextrose and glycerol solution are used as a liquid carrier of an injectable solution. Suitable excipients include light anhydrous silicic acid, crystalline cellulose, mannitol, starch, glucose, lactose, sucrose, gelatin, malt, rice, wheat flour, chalk, silica gel, sodium stearate, glyceryl monostearate, talc, sodium chloride, powdered skim milk, glycerol, propylene, glycol, water, ethanol, carmellose calcium, carmellose sodium, hydroxypropyl cellulose, hydroxypropyl methylcellulose, polyvinyl acetal diethylamino acetate, polyvinylpyrrolidone, gelatin, medium-chain fatty acid triglyceride, polyoxyethylene hydrogenated castor oil 60, saccharose, carboxymethylcellulose, corn starch, inorganic salt, and the like. When desired, the composition can contain a small amount of humectant or emulsifier or pH buffer. These compositions can be in a form of solution, suspension, emulsion, tablet, pill, capsule, powder, sustained release mixture, or the like. It is also possible to use traditional binding agents and carriers, such as tryglyceride, to prepare a composition as a suppository. Oral preparation can also comprise a standard carrier such as medicine grade mannitol, lactose, starch, magnesium stearate, sodium saccharin, cellulose, or magnesium carbonate. Examples of a suitable carrier are described in E. W. Martin, Remington's Pharmaceutical Sciences (Mark Publishing Company, Easton, U.S.A.) Such a composition contains a therapeutically effective amount of a therapeutic agent, preferably in a purified form, together with a suitable amount of carrier, such that the composition is provided in a form suitable for administration to a patient. A preparation must be suitable for the administration format. In addition, the composition may comprise, for example, a surfactant, excipient, coloring agent, flavoring agent, preservative, stabilizer, buffer, suspension, isotonizing agent, binding agent, disintegrant, lubricant, fluidity improving agent, corrigent, or the like.

Various tonicity adjusting agents can be used to adjust the tonicity of a composition. For an ophthalmic composition, a tonicity adjusting agent can be used to adjust the tonicity to that of a natural tear. For example, sodium chloride, potassium chloride, magnesium chloride, calcium chloride, dextrose, and/or mannitol can be added to a composition to approximate the tonicity to the physiological tonicity.

A suitable buffering system (e.g., sodium phosphate, sodium acetate, sodium citrate, sodium butyrate, or boric acid) can be added to a composition to prevent variation in pH under storage conditions.

An ophthalmic composition can comprise, in addition to a clathrated antioxidant, other components selected to temporarily alleviate a dry eye symptom and a dry eye condition by administration to the eye. Examples of other components include, but are not limited to, monomeric polyols (e.g., glycerol, propylene glycol, and ethylene glycol); polymeric polyols (e.g., polyethylene glycol, hydroxypropyl methyl cellulose ("HPMC"), carboxymethylcellulose sodium, hydroxypropyl cellulose ("HPC"), and dextran (e.g., Dextran 70)); water soluble proteins (e.g., gelatin); and vinyl polymers (e.g., polyvinyl alcohol, polyvinyl pyrrolidone, povidone, and carbamate (e.g., Carbomer 934P, Carbomer 941, Carbomer 940, and Carbomer 974P)).

A composition can comprise an antifouling agent for preservation. Examples of suitable antifouling agents include benzalkonium chloride, chlorobutanol, benzododecinium bromide, methylparaben, propylparaben, phenylethyl alcohol, disodium edetate, sorbic acid, polyquaternium-1, and other agents known to those skilled in the art. In addition, the composition of the invention can be sterilized.

As used herein, "therapy" refers to the prevention of exacerbation, preferably maintaining of the current state, more preferably alleviation, and still more preferably elimination of a disease or disorder (e.g., dry eye) when such a condition has developed, including being capable of exerting a prophylactic effect or an effect of improving a disease of a patient or one or more symptoms accompanying the disease. Preliminary diagnosis with suitable therapy may be referred to as "companion therapy" and a diagnostic drug therefor may be referred to as "companion diagnostic agent".

As used herein, "therapeutic drug (agent)" broadly refers to any agent capable of treating a condition of interest (e.g., ophthalmic diseases such as dry eye or the like). In one embodiment of the invention, a "therapeutic drug" may be a pharmaceutical composition comprising an active ingredient and one or more pharmacologically acceptable carriers. A pharmaceutical composition can be manufactured, for example, by mixing an active ingredient and the carriers by any method known in the technical field of pharmaceuticals. Further, usage mode of a therapeutic drug is not limited, as long as it is used for therapy. A therapeutic drug may be the active ingredient alone or a mixture of an active ingredient and any ingredient. Further, the shape of the carriers is not particularly limited. For example, the carrier may be a solid or liquid (e.g., buffer).

As used herein, "prevention (prophylaxis)" refers to the action of taking a measure against a disease or disorder (e.g., dry eye) from being in such a condition prior to being in such a condition. It is possible to use the agent of the invention to perform diagnosis, and optionally use the agent of the invention to prevent or take measures to prevent, for example, dry eye or the like.

As used herein, a "prophylactic drug (agent)" broadly refers to any agent capable of preventing a condition of interest (e.g., diseases such as dry eye or the like).

As used herein, a "patient" or "subject" in one embodiment of the invention includes humans or mammals excluding humans (e.g., one or more of mouse, guinea pig, hamster, rat, mouse, rabbit, pig, sheep, goat, cow, horse, cat, dog, marmoset, monkey, chimpanzee, and the like).

The pharmaceutical composition, therapeutic agent, or prophylactic agent of the invention can be provided as a kit. In a specific embodiment, the present invention provides an agent pack or kit comprising one or more containers filled with one or more ingredients of the composition or drug of the invention. Optionally, information indicating approval for manufacture, use, or sale for administration to humans by a government agency regulating the manufacture, use, or sale of drugs or biological products in a stipulated form can be appended to such a container.

As used herein, "kit" refers to a unit generally providing portions to be provided (e.g., therapeutic drug, prophylactic drug, each component thereof, manual, and the like) in two or more separate sections. The present invention can be provided as a kit that provides an active ingredient separately from a component for clathration. This form of a kit is preferred when a composition that should not be provided in a mixed state and is preferably mixed immediately before use for safety reasons or the like is intended to be provided. Preferably, such a kit advantageously comprises an instruction or manual describing how the provided portions (e.g., therapeutic drug and prophylactic drug) are used or how a reagent should be handled. When the kit herein is used as a reagent kit, the kit generally comprises an instruction describing how to use a therapeutic drug, prophylactic drug, and the like.

As used herein, "instruction" is a document explaining the method of use of the present invention for a physician or other users. The instruction has a description of the detection method of the invention, method of use of a diagnostic agent, or instruction to administer a drug or the like. Further, an instruction may have a description instructing administration to the eye (e.g., by injection, eye ointment, eye drops, or the like) as a site of administration. The instruction is prepared in accordance with a format specified by the regulatory agency of the country in which the invention is practiced (e.g., the Ministry of Health, Labor and Welfare in Japan, Food and Drug Administration (FDA) in the U.S., or the like), with an explicit description showing approval by the regulatory agency. The instruction is a so-called package insert and is typically provided in, but not limited to, paper media. The instructions can also be provided in a form such as electronic media (e.g., web sites provided on the Internet or emails).

The dose of the therapeutic agent of the invention can vary depending on the properties of a disorder or condition, but the dose can be determined by those skilled in the art with standard clinical techniques based on the descriptions in the present specification. It is also possible to use an in vitro assay to assist in identifying the optimal range of dosage as needed. Since an accurate dose to be used in a formulation can vary depending on the route of administration and the severity of a disease or disorder, the dose should be determined in accordance with the judgment of a physician and the condition of each patient. However, the dosage, while not particularly limited, may be, for example, 0.001, 1, 5, 10, 15, 100, or 1000 mg/kg body weight per dose or a value between any two such values. The interval of administration, while not particularly limited, may be for example one or two doses for every 1, 7, 14, 21, or 28 days, or one or two doses for a number of days between any two such values. The dosage, administration interval, and administration method may be appropriately selected depending on the age or body weight of a patient, symptom, target organ, or the like. A therapeutic drug preferably comprises a therapeutically effective dose or an effective dose of active ingredients at which a desired action is exerted. It may be determined that there is a therapeutic effect when a malignant tumor marker significantly decreases after administration. The effective dose can be estimated from a dose-response curve obtained from an in vitro or animal model testing system.

6. Preferred Embodiments

A preferred embodiment of the invention provides a composition comprising one or more antioxidants selected from: astaxanthin, canthaxanthin, zeaxanthin, β-carotene, lutein, lycopene, resveratrol, meso-zeaxanthin, EPA, DHA, curcumin, and vitamin E, clathrated with one or more host compounds selected from: cyclodextrin, arabinogalactan, glycyrrhizin, hydroxy-beta-cyclodextrin, β1,3-1,6-glucan, calixarene, cavitand, crown ether, calixarene, spherand, sulfobutyl ether-β-cyclodextrin, randomly methylated-β-cyclodextrin, hydroxy-γ-cyclodextrin, epichlorohydrin-β-cyclodextrin, and carboxymethyl epichlorohydrin-β-cyclodextrin.

Various combinations of clathrate compounds have been made and used as food products, beverages, household items, cosmetics, and the like. Those skilled in the art can select a suitable host compound by utilizing structural information or the like in accordance with a guest compound (Ryuji FUJIWARA, Journal of the Crystallographic Society of Japan, Vol. 24 (1982) No. 1, p 54-64; Shikurodekirutorin no Oyogijutsu [Applied technology of cyclodextrin] CMC Publishing, Supervised by: Keiji TERAO, Makoto KOMIYAMA, published in February 2008).

In a preferred embodiment of the invention, the composition is for increasing the tear volume, increasing the goblet cell count, increasing mucin, or treating or preventing dry eye or a similar ophthalmic disease, conjunctivitis, corneal ulcer, age-related macular degeneration, cataract, pseudoexfoliation syndrome, immunological diseases including GVHD, and symptoms improved by increasing the tear volume and/or goblet cells and/or mucin in such diseases. The composition can also be for recovery of the ocular surface after an invasive ophthalmic procedure including LASIK, cataract surgery, and the like.

One embodiment of the invention is a composition comprising a lipid-soluble antioxidant clathrated with a cyclic polysaccharide. Another embodiment of the invention is a composition comprising a carotenoid clathrated with a cyclic polysaccharide. Another embodiment of the invention is a composition comprising xanthophyll clathrated with a cyclic polysaccharide. Another embodiment of the invention is a composition comprising astaxanthin clathrated with a cyclic polysaccharide.

A composition comprising astaxanthin clathrated with cyclodextrin is particularly preferable, as it is shown to be particularly useful in therapy of an ophthalmic disease (especially dry eye) in the Examples herein.

Another embodiment of the invention provides a method of manufacturing a composition comprising an antioxidant, comprising clathrating the antioxidant. Clathration can be performed using any host compound described in other portions herein by using any antioxidant described in other portions herein. A composition to be manufactured can comprise any feature described in other portions herein. For example, the composition can be a composition for any application described in other portions herein (e.g., increasing the tear volume, increasing the goblet cell count, increasing mucin, or treating or preventing an ophthalmic disease). Examples of ophthalmic diseases include dry eye or similar ophthalmic diseases, conjunctivitis, corneal ulcer, age-related macular degeneration, cataract, and the like.

Another embodiment of the invention provides a method of increasing a tear volume, increasing a goblet cell count, increasing mucin, or treating or preventing an ophthalmic disease, comprising administering a clathrated antioxidant. The ophthalmic disease can be dry eye or similar ophthalmic diseases, conjunctivitis, corneal ulcer, age-related macular degeneration, or cataract. Administration of a clathrated antioxidant includes administration in a form of a composition in any dosage form described herein. The route of administration can be selected from ocular injection, topical application (including application to an eye), eye drop, intravenous injection, intravenous drip, oral administration, parenteral administration, transdermal administration, and the like.

Reference literatures such as scientific literatures, patents, and patent applications cited herein are incorporated herein by reference to the same extent that the entirety of each document is specifically described.

As described above, the present invention has been described while showing preferred embodiments to facilitate understanding. The present invention is described hereinafter based on Examples. The above descriptions and the following Examples are not provided to limit the present invention, but for the sole purpose of exemplification. Thus, the scope of the present invention is not limited to the embodiments and Examples specifically described herein and is limited only by the scope of claims.

EXAMPLES

Manufacturing Example 1: Preparation of CD Clathrated ASX

[Preparation]

Astaxanthin (Sigma-aldrich) was clathrated and solubilized by the following procedure using γ-cyclodextrin (Tokyo Chemical Industry). The procedure is described hereinafter.

Astaxanthin and γ-cyclodextrin were admixed well after measuring out an amount required at a molar ratio by mass of 2:1. 1 mL of Milli-Q was then added per 1 mg of astaxanthin, and the mixture was stirred with an ultrasonic homogenizer (amplitude 20%, pulse oscillation for 1 second at a 2 second interval) under conditions of 4° C. for 30 minutes. The mixture was further treated from 4 hours to overnight with a shaker or stirrer (100 to 150 rpm). The mixture was then stirred with an ultrasonic vessel or ultrasonic homogenizer (amplitude 20%, pulse oscillation for 1 second at a 2 second interval) under conditions of 4° C. for 30 minutes, and centrifuged for 20 minutes at 20° C. at 5000 to 7000 rpm to remove insoluble materials. The final clathrate was obtained by filtration with an aqueous 0.45 μm filter.

[Solubilization Testing]

A liquid prepared by suspending or dissolving astaxanthin was filtered by the following procedure to test whether astaxanthin was solubilized. Since astaxanthin exhibits color in a visible region, the liquid would be colorless when astaxanthin is removed from the solution (not dissolved). Thus, the solubilization can be determined. The astaxanthin concentration in the filtrate can be measured by measuring the absorbance of the wavelength 478 nm using an absorption (spectrophoto)meter.

While astaxanthin can be dissolved in an organic solvent such as DMSO because astaxanthin is a lipid-soluble substance, astaxanthin cannot be dissolved in an aqueous solvent that does not have an organic solvent, so that astaxanthin is removed by filtration to produce a colorless filtrate (FIG. 1). However, it was confirmed that clathrated astaxanthin using γ-cyclodextrin was solubilized, as it remained in an aqueous solution even after filtration The concentration of astaxanthin dissolved in water was measured by the following method. Astaxanthin was dissolved in DMSO, and the final concentration was adjusted to 6.25, 12.5, 25, 50, and 100 μg/ml with Milli-Q water. After 0 point correction with a solvent, 480 nm absorbance of each astaxanthin solution was measured, and calibration curves were drawn. The concentration of water soluble astaxanthin solution was found from the 480 nm absorbance measurement value of the water soluble astaxanthin solution based thereon.

In addition to confirmation of the liquid color by visual inspection, clathration can be confirmed/quantified by measuring absorbance or HPLC analysis.

Manufacturing Example 2: Preparation of Arabinogalactan Clathrated Astaxanthin

Astaxanthin was clathrated by the following procedure using arabinogalactan as the host.

Astaxanthin and arabinogalactan were admixed well after measuring out an amount required at a mass ratio of 4:1. 1 mL of Milli-Q was then added per 1 mg of astaxanthin, and the mixture was stirred with an ultrasonic homogenizer (amplitude 20%, pulse oscillation for 1 second at a 2 second interval) under conditions of 4° C. for 30 minutes. The mixture was further treated from 4 hours to overnight with a shaker or stirrer (100 to 150 rpm) at room temperature. The mixture was then stirred with an ultrasonic vessel or ultrasonic homogenizer (amplitude 20%, pulse oscillation for 1 second at a 2 second interval) under conditions of 4° C. for 30 minutes, and centrifuged for 20 minutes at 20° C. at 5000 to 7000 rpm to remove insoluble matters. The final clathrate was obtained by filtration with an aqueous 0.45 μm filter.

Manufacturing Example 3: Preparation of Clathrate Compounds of Different Combinations Lutein is clathrated by the following procedure using glycyrrhizin as the host.

Glycyrrhizin and lutein are admixed well after measuring out an amount required at a mass ratio of 4:1. 1 mL of Milli-Q is then added per 1 mg of lutein, and the mixture is stirred with an ultrasonic homogenizer (amplitude 20%, pulse oscillation for 1 second at a 2 second interval) under conditions of 4° C. for 30 minutes. The mixture is further treated from 4 hours to overnight at room temperature with a shaker or stirrer (100 to 150 rpm). The mixture is then stirred with an ultrasonic vessel or ultrasonic homogenizer (amplitude 20%, pulse oscillation for 1 second at a 2 second interval) under conditions of 4° C. for 30 minutes, and centrifuged for 20 minutes at 20° C. at 5000 to 7000 rpm to remove insoluble matters. The final clathrate is obtained by filtration with an aqueous 0.45 μm filter.

Canthaxanthin is clathrated by the following procedure using hydroxy-beta-cyclodextrin as the host.

Hydroxy-beta-cyclodextrin and canthaxanthin are admixed well after measuring out an amount required at a mass ratio of 2:1. 1 mL of Milli-Q is then added per 1 mg of canthaxanthin, and the mixture was stirred with an ultrasonic homogenizer (amplitude 20%, pulse oscillation for 1 second at a 2 second interval) under conditions of 4° C. for 30 minutes. The mixture is further treated from 4 hours to overnight at room temperature with a shaker or stirrer (100 to 150 rpm). The mixture is then stirred with an ultrasonic vessel or ultrasonic homogenizer (amplitude 20%, pulse oscillation for 1 second at a 2 second interval) under conditions of 4° C. for 30 minutes, and centrifuged for 20 minutes at 20° C. at 5000 to 7000 rpm to remove insoluble matters. The final clathrate is obtained by filtration with an aqueous 0.45 μm filter.

Astaxanthin is clathrated by the following procedure using hydroxypropyl-gamma-cyclodextrin as the host.

Hydroxypropyl-gamma-cyclodextrin and astaxanthin are admixed well after measuring out an amount required at a mass ratio of 3:1. 1 mL of Milli-Q is then added per 1 mg of astaxanthin, and the mixture is stirred with an ultrasonic homogenizer (amplitude 20%, pulse oscillation for 1 second at a 2 second interval) under conditions of 4° C. for 30 minutes. The mixture is further treated from 4 hours to overnight at room temperature with a shaker or stirrer (100 to 150 rpm). The mixture is then stirred with an ultrasonic vessel or ultrasonic homogenizer (amplitude 20%, pulse oscillation for 1 second at a 2 second interval) under conditions of 4° C. for 30 minutes, and centrifuged for 20 minutes at 20° C. at 5000 to 7000 rpm to remove insoluble matters. The final clathrate is obtained by filtration with an aqueous 0.45 μm filter.

Example 1: Healing Effect of Astaxanthin Eye Drops on Dry Eye Symptom

[Overview]

The objective of this Example was to study the effect of improvement of astaxanthin eye drops on a dry eye symptom.

[Materials and Methods]

Astaxanthin was solubilized by clathration with γ-cyclodextrin in accordance with Manufacturing Example 1 and used as water-soluble astaxanthin (also denoted as wsAsx).

As a preliminary matter, antioxidant capability of water soluble astaxanthin was studied in cultured cells (mouse brain tumor derived SR-CDF1 DBT cells, JCRB Cell Bank). Oxidative stress was induced with 300 μM of $H_2O_2$ in the cultured cells, and the reactive oxygen group was detected using a DCFDA reagent. More specifically, $2.5 \times 10^4$ DBT cells were seeded on an 8 well culture slide, and wsAsx was added at the same time. After 42 to 48 hours, a DCFDA reagent was added at a final concentration of 100 μM and allowed to be taken into the cells, and the production of ROS was induced with 300 μm of $H_2O_2$.

A dry eye mouse model was created by eye drop treatment with benzalkonium chloride (also denoted as BAC).

After two weeks of continuous BAC treatment of mice, additional BAC treatment and eye drop treatment with water soluble astaxanthin or water soluble control (vehicle, γ-cyclodextrin only) were continued for two weeks. A group of mice applied with only PBS eye drops was used as a positive control.

The change in the tear volume in the mouse model was measured by Schirmer's test. The tear volume was determined as a relative tear volume (normal tear volume (filter moving distance): 7.17±1.35 mm) when normal tear volume was 100. Statistical processing: ANOVA, Student's t-test.

To find the effect of astaxanthin eye drops on ocular surface goblet cells of a dry eye mouse model, histological analysis was performed after two weeks of astaxanthin eye drops, and the number of goblet cells was counted by counting the cells stained red by PAS stain.

[Results]

Figure 2:
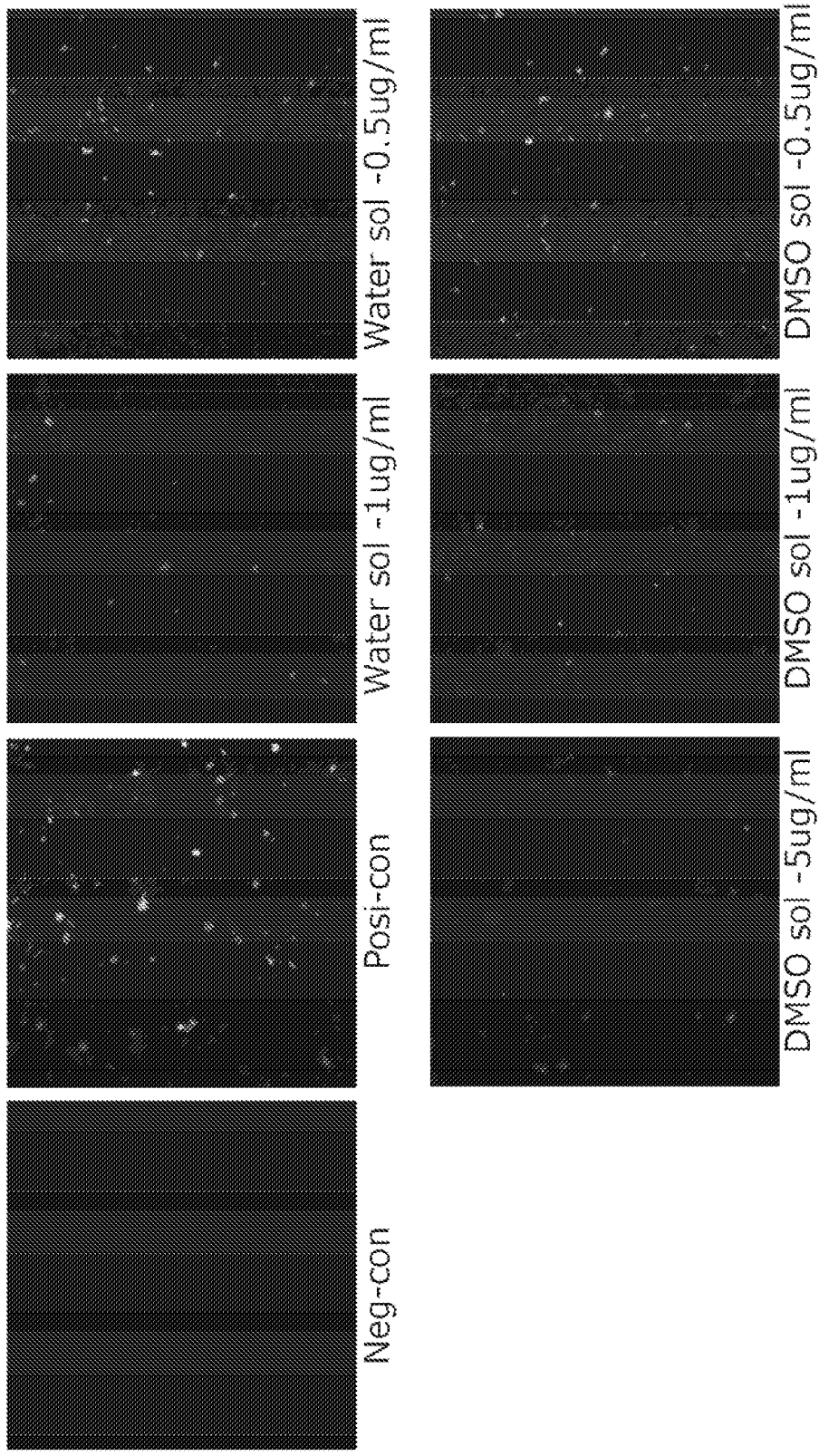
FIG. 2 is a diagram showing the antioxidant capability of astaxanthin. Reactive oxygen species was detected using a DCFDA reagent, and the antioxidant capability of the shown test substances (Neg-con: (untreated group . . . no treatment is applied), Posi-con: (production of reactive oxygen is detected under hydrogen peroxide stimulation), Water sol: astaxanthin solubilized by cyclodextrin clathration, and DMSO sol: astaxanthin dissolved in DMSO) was studied. Low fluorescence indicates that the antioxidant capability of a test substance against oxidative stress induced by hydrogen peroxide is high.

As shown in FIG. 2, astaxanthin clathrated with cyclodextrin had sufficient antioxidant capability (FIG. 2).

Figure 3:
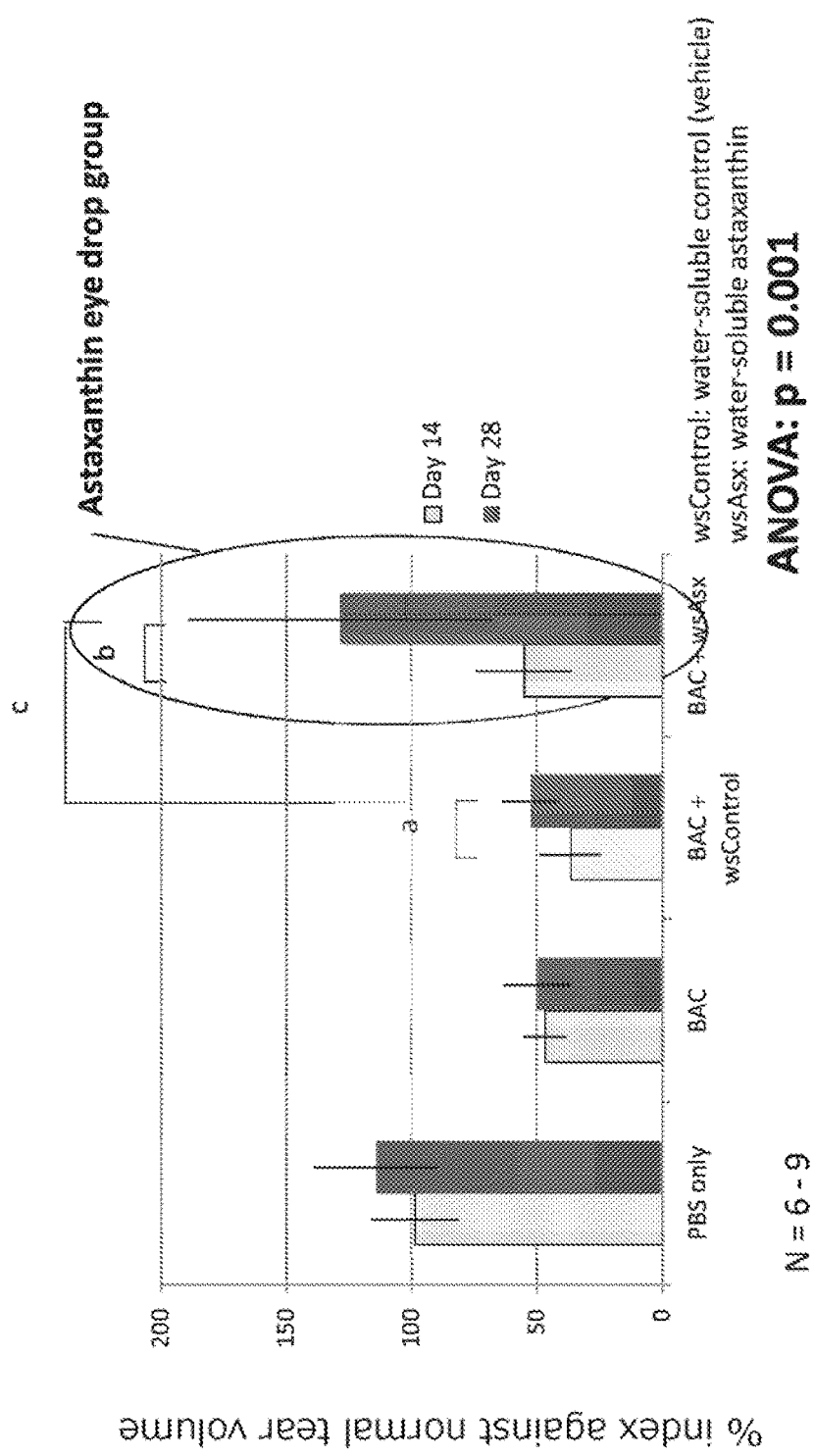
FIG. 3 is a diagram showing the change in tear volume of a mouse with dry eye by dropping astaxanthin in the eyes. The vertical axis indicates a relative value with respect to the normal tear volume. The tear volumes on day 14 (point in time after two weeks of BAC treatment) and day 28 (point in time after two weeks of each treatment) are shown for each treatment group. In the figure, "wsControl" is the water-soluble control (vehicle), "wsAsx" is water-soluble astaxanthin (ASX), and "BAC" is benzalkonium chloride.

The results in the mouse model are shown in FIGS. 3 and 4. As shown in FIG. 3, the tear volume was decreased by about a half in a dry eye mouse model (BAC+0.02% BAC), but the tear volume of a dry eye mouse recovered to the normal volume with two weeks of astaxanthin eye drops. Day 14: immediately after creation of BAC dry model (before treatment); Day 28: after astaxanthin eye drops every day for 14 days to a dry eye model) a, b: Day 14 vs Day 28 Student's t-test: P<0.05; c: wsControl at Day 28 vs wsAsx Day 28 Student's t-test: P<0.05.

As shown in FIG. 4, the goblet cell count significantly decreased in a dry eye model, but the goblet cell count recovered to the same level as the normal count by astaxanthin eye drops (**Student's t-test P<0.01). Goblet cells are cells that produce mucin, which is essential for creating the tear structure. Mucin of a mucosal liquid secreted from goblet cells (secreted mucin) serves an important role in the stability of tears by distributing tears on the surface of an eye uniformly and retaining tears on the surface of the eye.

These results show that use of a lipid-soluble antioxidant astaxanthin as eye drops is useful in increasing the tear volume or increasing the goblet cell count. Therefore, the results show that use of a lipid-soluble antioxidant astaxanthin as an ophthalmic drug is useful in the therapy or prevention of dry eye or similar ophthalmic disease.

Example 2: Comparison and Examination of Astaxanthin Eye Drops and Astaxanthin Supplement for Dry Eye Symptom

[Overview]

The objective of this Example was to study the effect of improvement of a dry eye symptom when astaxanthin eye drops are applied and when astaxanthin is orally administered.

[Materials and Method]

A dry eye mouse model was created in the same manner described in Example 1. Subsequently, astaxanthin eye drops were applied and astaxanthin was orally administered (oral intake astaxanthin, also denoted as oAsx) for two weeks. The change in tear volume was measured by Schirmer's test in the same manner as Example 1. The goblet cells were also counted in the same manner as Example 1.

[Results]

Figure 5:
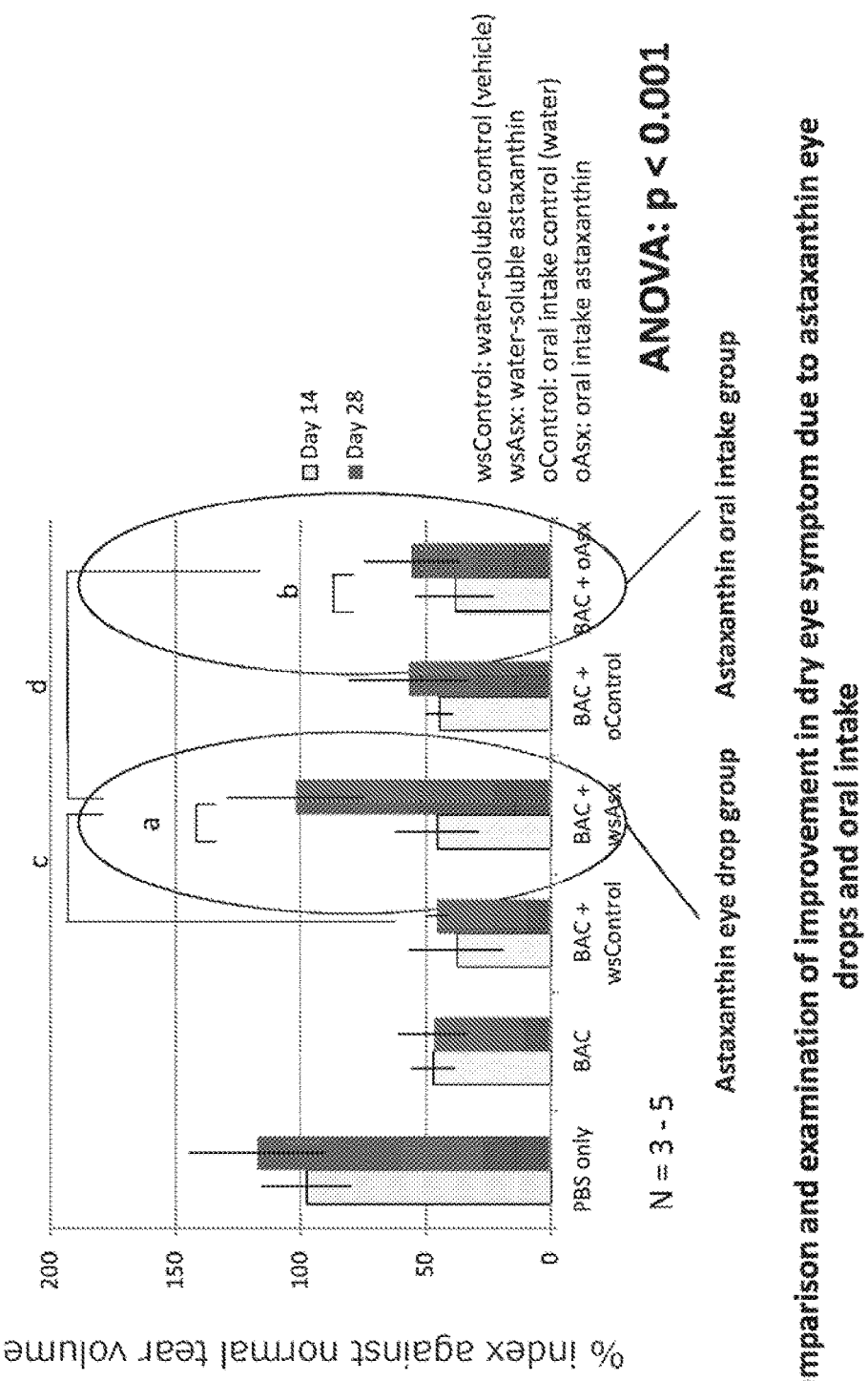
FIG. 5 is a diagram showing the change in tear volume of a dry eye mouse due to astaxanthin eye drop and oral administration. The vertical axis is a relative value with respect to the normal tear volume. The tear volumes on day 14 (point in time after two weeks of BAC treatment) and day 28 (point in time after two weeks of each treatment) are shown for each treatment group. In the figure, "wsControl" is the water-soluble control (vehicle), "wsAsx" is water-soluble astaxanthin (ASX), "oControl" is an oral intake control (water), "oAsx" is oral intake astaxanthin, and "BAC" is benzalkonium chloride.

The results are shown in FIGS. 5 and 6. As shown in FIG. 5, the tear volume of a dry eye mouse recovered to the normal value with 2 weeks of astaxanthin eye drops (1 μg/ml), but the tear volume increased only slightly in the oral intake group (200 mg/kg) and no significant change was observed.

Day 14: before starting treatment (immediately after creation of BAC dry model; Day 28: after astaxanthin eye drops every day for 14 days to a dry eye model) a: wsAsx at Day 14 vs wsAsx at Day 28 Student's t test $P<0.01$; b: oAsx at Day 14 vs oAsx at Day 28 Student's t test $P<0.05$; c: wsControl at Day 28 vs ws Asx at Day 28 $P<0.05$; d: wsAsx at Day 28 vs oAsx at Day 28 $P<0.01$. The goblet cell count also recovered to the same level as the normal count by water-soluble astaxanthin eye drops in histological analysis of goblet cells. Meanwhile, recovery in the goblet cell count was not observed in the oral administration group (statistical processing: ANOVA, Student's t-test, a, b, c, d, e: $P<0.001$) (FIG. 6).

It can be understood from the results in this Example that direct application to the eye, rather than oral administration, of water-soluble and lipid-soluble antioxidant including water soluble astaxanthin is advantageous in increasing the tear volume and increasing the goblet cell count, and is thus advantageous for treating or preventing dry eye or similar ophthalmic disease.

Example 3: Examination of Superiority of Water-Soluble Astaxanthin

[Overview]

The objective of this Example was to examine the usefulness of astaxanthin that is water-solubilized and used and astaxanthin that is emulsified or dissolved in an organic solvent for the improvement of a dry eye symptom.

[Materials and Methods]

Water-soluble astaxanthin was prepared by clathration with γ-cyclodextrin in the same manner as Example 1. Emulsified astaxanthin was prepared using tween 80 as a surfactant. Astaxanthin was dissolved using DMSO as an organic solvent.

As a preliminary experiment, the effect of these specimens on the growth of mouse DBT cells was studied. Astaxanthin that was dissolved in DMSO, emulsified, or water-solubilized was added to $4\times10^4$ DBT cells to perform a 48 hour cell growth test. The factor of growth of the cell count after 48 hours was measured, with $4\times10^4$ as the baseline.

A dry eye mouse model was created in the same manner as Example 1. Subsequently, water-soluble astaxanthin eye drops and DMSO dissolved astaxanthin eye drops were applied for two weeks, and the change in the tear volume was measured by Schirmer's test in the same manner as Example 1. The goblet cells were also counted in the same manner as Example 1. Since cell growth was dramatically suppressed with emulsified astaxanthin (FIG. 7), this was not studied in a dry eye mouse model.

[Results]

Figure 7:
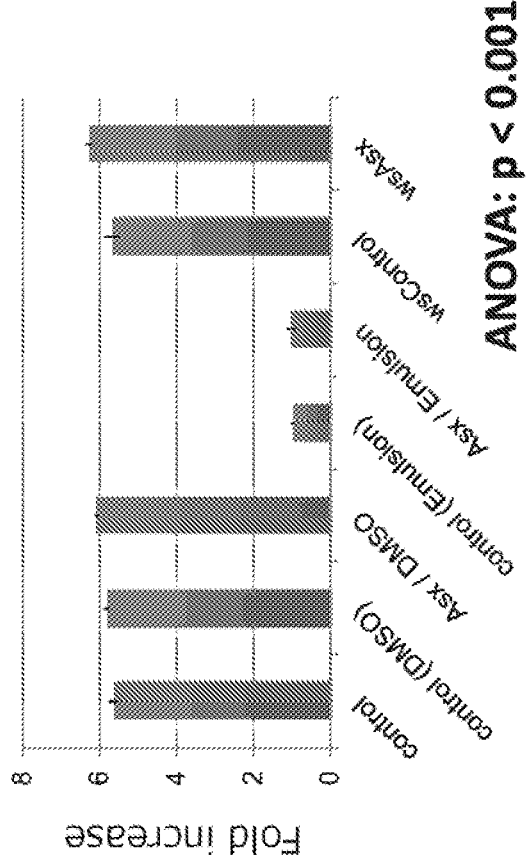
FIG. 7 is a diagram showing the effect of ASX dissolved in various solvents on cell growth in mouse DBT cells. The vertical axis indicates the multiple of increase in the mouse DBT cell count.
Figure 8:
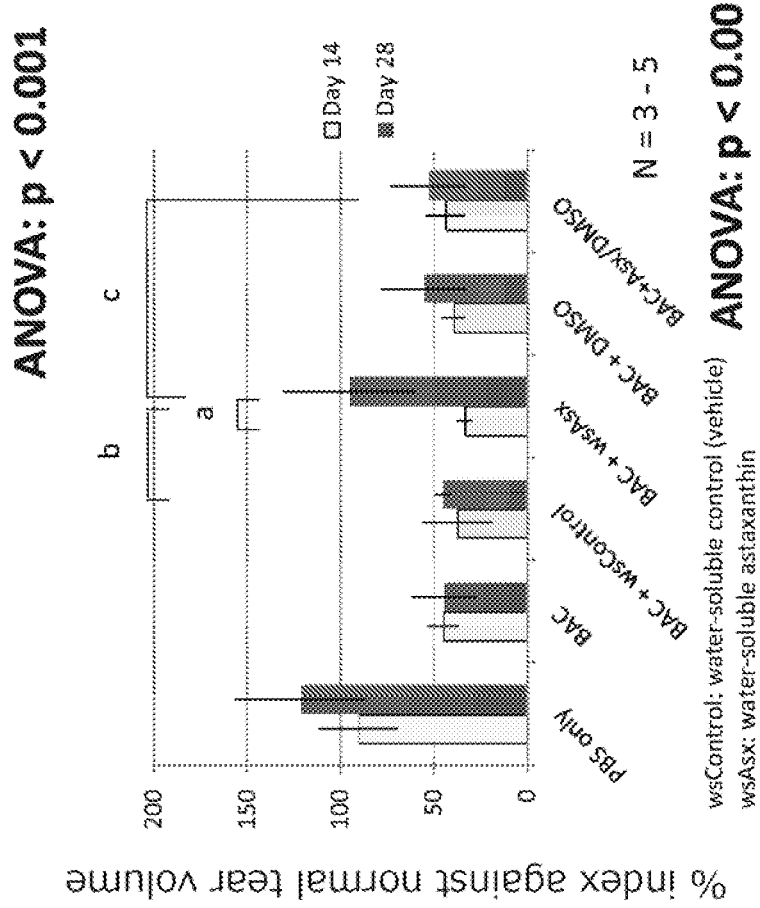
FIG. 8 is a diagram showing the change in the tear volume of a dry eye mouse due to water-soluble astaxanthin eye drop, DMSO-dissolved astaxanthin eye drop, and astaxanthin oral administration. The vertical axis is the relative value with respect to normal tear volume. The tear volumes on day 14 (point in time after two weeks of BAC treatment) and day 28 (point in time after two weeks of each treatment) are shown for each treatment group.

The results are shown in FIGS. 7 and 8. The results for goblet cell count is shown in FIG. 6 with the results of Example 2.

As shown in FIG. 7, cell growth was dramatically suppressed with emulsified astaxanthin, but an effect on cell growth was not exhibited with water soluble astaxanthin and DMSO dissolved astaxanthin.

As shown in FIG. 8, with eye drops of water-soluble astaxanthin or DMSO (0.1%) dissolved astaxanthin, an effect of improvement in dry eye was observed with water-soluble astaxanthin, but not with DMSO dissolved astaxanthin. Statistical processing: ANOVA and Student's t-test, a: wsAsx at Day 14 vs wsAsx at Day 28 $P<0.05$; b: wsControl at Day 28 vs wsAsx at Day 28 $P<0.05$; c: wsAsx at Day 28 vs Asx/DMSO at Day 28 $P<0.05$.

In the histological analysis of goblet cells, the goblet cell count recovered to the same level as the normal count with water-soluble astaxanthin eye drops. Meanwhile, recovery in the goblet cell count was not observed with DMSO-dissolved astaxanthin (statistical processing: ANOVA, Student's t-test, a, b, c, d, e: $P<0.001$) (FIG. 6).

Although not to be bound by any theory, the results show that clathration of astaxanthin using γ-cyclodextrin instead of astaxanthin alone is unexpectedly useful in improving dry eye.

Example 4: Examination of Arabinogalactan Clathrate

[Overview]

The objective of this Example was to examine the usefulness of using astaxanthin that is water-solubilized with arabinogalactan.

[Materials and Methods]

In this Example, astaxanthin was water-solubilized by clathration using arabinogalactan (Arb) as described in Manufacturing Example 2.

Astaxanthin clathrated using Arb was added to $4\times10^4$ DBT cells to perform a 48 hour cell growth test in the same manner as Example 3. The factor of growth of the cell count after 48 hours was measured, with $4\times10^4$ as the baseline.

Next, the antioxidative force was tested in the same manner as Example 1 by using astaxanthin clathrated with arabiogalactan in the same manner as Example 1. More specifically, astaxanthin clathrated with Arb was added to DBT cultured cells, and oxidative stress was induced with 300 μM of $H_2O_2$, and reactive oxygen species were detected with a DCFDA reagent.

[Results]

Figure 9:
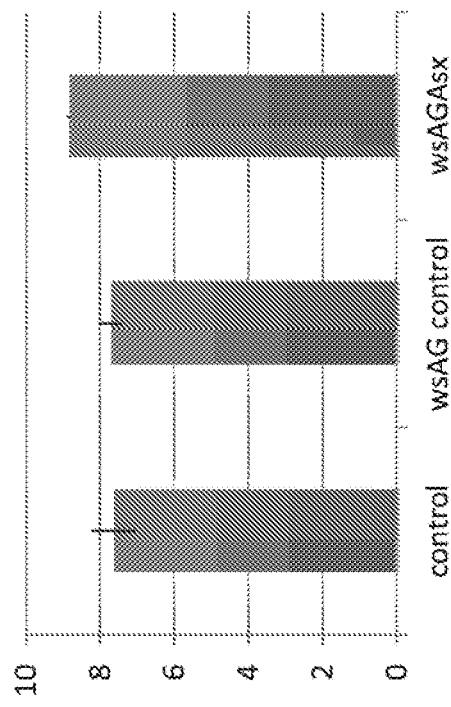
FIG. 9 is a diagram showing the effect of water-soluble astaxanthin using different host compounds on cell growth. The vertical axis indicates the multiple of increase in mouse DBT cells.

The results are shown in FIG. 9. It was demonstrated that clathration using Arb does not have an adverse effect on cell growth in the same manner as clathration using γ-cyclodextrin. It was also revealed that astaxanthin clathrated with Arb has sufficient antioxidant capability as shown in FIG. 10.

Therefore, it is understood that a lipid-soluble antioxidant that is clathrated with Arb is also useful in treating or preventing dry eye or similar ophthalmic disease in the same manner as using γ-cyclodextrin.

Example 5: Examination of Clathration of Other Antioxidants

[Overview]

This Example examined clathration of lipid-soluble antioxidants other than astaxanthin.

[Materials and Methods]

Lycopene and canthaxanthin were clathrated with γ-cyclodextrin in the same manner as Manufacturing Example 1. Solubilization of lycopene and canthaxanthin was confirmed by filtration with a 0.45 μm filter.

Clathrated lycopene was confirmed to have antioxidant capability in the same manner described in Example 1. More specifically, oxidative stress was induced with 200 μM of $H_2O_2$ in cultured cells, and reactive oxygen species were detected using a DCFDA reagent.

[Results]

The results are shown in FIGS. 11 and 12. The solution after filtration was colored by lycopene. Thus, it was confirmed that lycopene was water-solubilized (FIG. 11b). Furthermore, water-soluble lycopene was confirmed to have antioxidant capability, albeit weaker than that of water soluble astaxanthin (FIG. 11c). Successful water-solubilization of canthaxanthin was also confirmed by visual inspection with the manifested color of the solution after filtration (FIG. 12).

It was shown that lipid-soluble antioxidants other than astaxanthin can be water-solubilized by clathration with γ-cyclodextrin. It was also shown that antioxidant capability is maintained after water-solubilization. Therefore, it is understood that use of other lipid-soluble antioxidants instead of astaxanthin is also useful in treating or preventing dry eye or similar ophthalmic disease in the same manner as the use of astaxanthin.

Example 6: Effect of Other Clathrate Compounds on Dry Eye Symptom

[Overview]

The effect on a dry eye symptom is tested in the same manner as Example 1 by using the clathrate prepared in Manufacturing Examples 2 and 3.

A dry eye mouse model is prepared by treatment with benzalkonium chloride-containing eye drop.

After continuous BAC treatment of mice for two weeks, additional BAC treatment or eye drop treatment with each antioxidant clathrated with each host compound or water-soluble control (only host compound) is continued for two weeks. A group of mice applied with only eye drop of PBS is used as a positive control.

A change in the tear volume in the mouse model is measured by Schirmer's test. The tear volume is determined as a relative tear volume (normal tear volume (filter moving distance): 7.17±1.35 mm) when normal tear volume is 100. Statistical processing: ANOVA, Student's t-test. To find the effect of astaxanthin eye drops on ocular surface goblet cells of a dry eye mouse model, histological analysis is performed after two weeks of astaxanthin eye drops, and the number of goblet cells is counted by counting the cells stained red by PAS stain.

[Results]

The tear volume of the mouse model recovers to the normal volume by eye drops of clathrated astaxanthin, with arabinogalactan as the host compound. The goblet cell count also recovers to the same level as the normal count.

The tear volume of the mouse model recovers to the normal volume by eye drops of clathrated resveratrol, with calixarene as the host compound. The goblet cell count also recovers to the same level as the normal count.

The tear volume of the mouse model recovers to the normal volume by eye drops of clathrated lutein, with glycyrrhizin as the host compound. The goblet cell count also recovers to the same level as the normal count.

The tear volume of the mouse model recovers to the normal volume by eye drops of clathrated canthaxanthin, with hydroxy-beta-cyclodextrin as the host compound. The goblet cell count also recovers to the same level as the normal count.

The tear volume of the mouse model recovers to the normal volume by eye drops of clathrated resveratrol, with calixarene as the host compound. The goblet cell count also recovers to the same level as the normal count.

The tear volume of the mouse model recovers to the normal volume by eye drops of clathrated zeaxanthin with β1,3-1,6-glucan as the host compound. The goblet cell count also recovers to the same level as the normal count.

The tear volume of the mouse model recovers to the normal volume by eye drops of clathrated astaxanthin, with hydroxypropyl-gamma-cyclodextrin as the host compound. The goblet cell count also recovers to the same level as the normal count.

Example 7: Example of Preparation of Formulations

Examples of Preparation of Eye Drops

The composition of the test substance at each concentration is shown below.

| | |
|---|---|
| Clathrated astaxanthin (clathrated astaxanthin is manufactured by the method used in the Manufacturing Examples or a modified method thereof) | 0.1 g (astaxanthin weight) |
| Sodium chloride | 0.85 g |
| Sodium dihydrogenphosphate dihydrate | 0.1 g |
| Benzalkonium chloride | 0.005 g |
| Sodium hydroxide | appropriate amount |
| Purified water | appropriate amount |
| | Total amount of 100 ml (pH 7.0) |

While the content of active ingredients is denoted by the weight of the antioxidant, the content can be similarly denoted by the weight of the clathrated antioxidant.

Eye drops can also be diluted with a base.

The composition of the base is the following.

| | |
|---|---|
| Sodium chloride | 0.85 g |
| Sodium dihydrogenphosphate dihydrate | 0.1 g |
| Benzalkonium chloride | 0.005 g |
| Sodium hydroxide | appropriate amount |
| Purified water | appropriate amount |
| | Total amount of 100 ml (pH 7.0) |

(Note)

As described above, the present invention is exemplified by the use of its preferred embodiments. However, it is understood that the scope of the present invention should be interpreted solely based on the Claims. It is also understood that any patent, any patent application, and any references cited herein should be incorporated herein by reference in the same manner as the contents are specifically described herein.

RELATED APPLICATION

The present application claims priority to Japanese Patent Application No. 2017-123224 filed on Jun. 23, 2017. The entire content thereof is incorporated herein by reference for any purpose.

INDUSTRIAL APPLICABILITY

The present invention can be used as a novel drug for therapy of an ophthalmic disease.

The invention claimed is:

1. A method for treating or preventing an ophthalmic disease, ophthalmic disorder, or ophthalmic symptom in a subject, comprising administering an effective amount of astaxanthin clathrated with cyclodextrin to the subject.

2. The method of claim 1, wherein
the cyclodextrin is α-cyclodextrin.

3. The method of claim 1, wherein
a molar ratio of the astaxanthin and the cyclodextrin by mass is 2:1.

4. The method of claim 1, wherein
the ophthalmic composition further includes sodium chloride, sodium dihydrogenphosphate dihydrate, benzalkonium chloride and sodium hydroxide.

* * * * *